United States Patent [19]

Baumann

[11] Patent Number: 5,514,685

[45] Date of Patent: May 7, 1996

[54] HETEROATOM-CONTAINING TRICYCLIC COMPOUNDS

[75] Inventor: Karl Baumann, Vienna, Austria

[73] Assignee: Sandoz Ltd., Basel, Switzerland

[21] Appl. No.: 441,492

[22] Filed: May 15, 1995

Related U.S. Application Data

[63] Continuation of Ser. No. 58,508, May 6, 1993, abandoned.

[30] Foreign Application Priority Data

| May 7, 1992 | [GB] | United Kingdom | 9209815 |
| Mar. 10, 1993 | [GB] | United Kingdom | 9304927 |

[51] Int. Cl.$^6$ .............. A61K 31/435; A61K 31/40; C07D 273/01
[52] U.S. Cl. .............. 514/285; 546/63; 546/92; 546/112; 546/14; 548/428; 548/453; 548/423; 548/110; 514/291; 514/299; 514/411; 514/413; 514/410; 514/63
[58] Field of Search .............. 546/92, 112, 63; 548/428, 453, 423; 514/291, 299, 411, 413, 410, 285

[56] References Cited

U.S. PATENT DOCUMENTS

| 5,254,562 | 10/1993 | Okuhara et al. | 514/291 |
| 5,260,301 | 11/1993 | Nakanishi et al. | 514/291 |

FOREIGN PATENT DOCUMENTS

| 0184162 | 6/1986 | European Pat. Off. . |
| 0364031 | 4/1990 | European Pat. Off. . |
| 0364032 | 4/1990 | European Pat. Off. . |
| 0402931 | 12/1990 | European Pat. Off. . |
| 0413532 | 2/1991 | European Pat. Off. . |
| 0428365 | 5/1991 | European Pat. Off. . |
| 0480623 | 4/1992 | European Pat. Off. . |
| 2246350 | 1/1992 | United Kingdom . |
| WO9213862 | 8/1992 | WIPO . |
| WO9304680 | 3/1993 | WIPO . |

OTHER PUBLICATIONS

Official Gazette—Jan. 16, 1990 p. 1384, USP 4,894,366.
European Search Report, EP 93 81 0325 (Aug. 1993).

*Primary Examiner*—Johann Richter
*Assistant Examiner*—Laura R. Cross
*Attorney, Agent, or Firm*—Robert S. Honor; Melvyn M. Kassenoff; Thomas O. McGovern

[57] ABSTRACT

The invention concerns the compounds of formulae

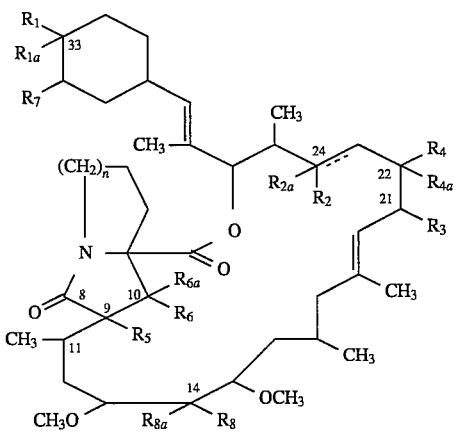

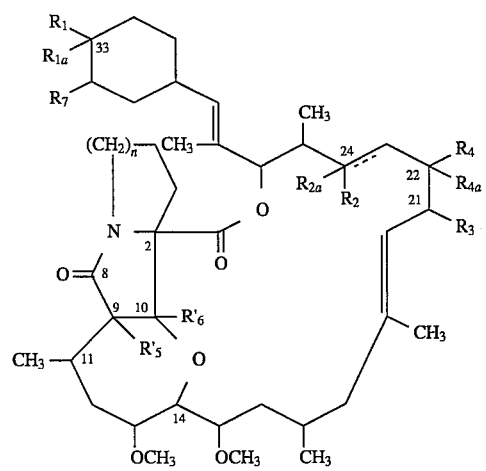

and

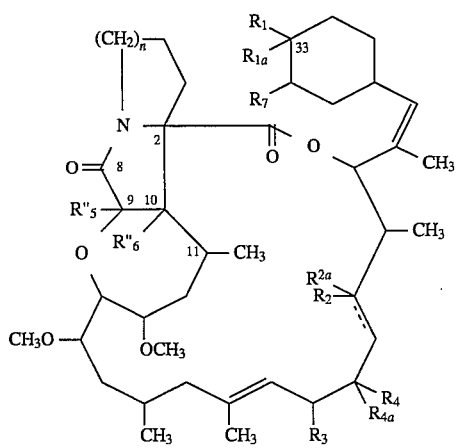

wherein the substituents have various significances. They can be prepared by various methods, e.g. acylation, reduction, alkylation, etc. They are indicated for use as pharmaceuticals, in particular as immunosuppressant, antiproliferative and antiinflammatory agents.

15 Claims, No Drawings

HETEROATOM-CONTAINING TRICYCLIC COMPOUNDS

This is a continuation of application Ser. No. 08/058,50, filed May 6, 1993 now abandoned.

The invention relates to the field of macrolides. It concerns the compounds of formulae I to III

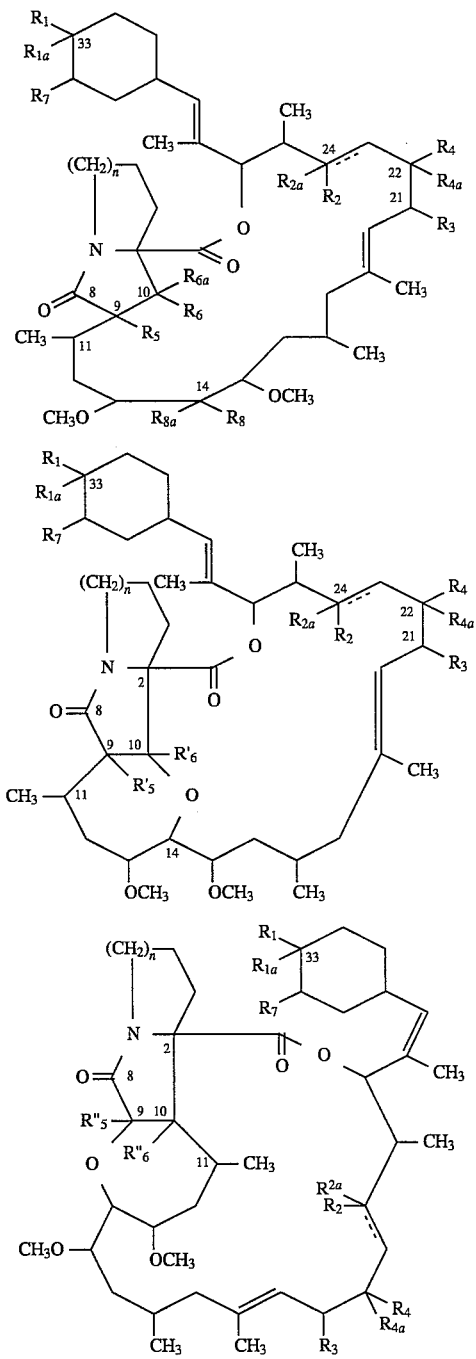

wherein the symbol ═══ represents a single bond or, when $R_{2a}$ is absent, a double bond;

$R_1$ represents an optionally protected hydroxy group and $R_{1a}$ represents hydrogen;

or $R_1$ and $R_{1a}$ together represent oxo;

$R_2$ represents an optionally protected hydroxy group or together with $R_4$ forms the —OC(═O)O— group, and $R_{2a}$ represents hydrogen or is absent;

whereby when the symbol ═══ is a single bond, $R_2$ together with $R_{2a}$ also represents oxo;

$R_3$ represents methyl, ethyl, n-propyl or allyl;

$R_4$ represents optionally protected hydroxy or together with $R_2$ forms the —OC(═O)O— group, and $R_{4a}$ represents hydrogen;

or $R_4$ together with $R_{4a}$ represents oxo;

$R_5$ represents alkoxycarbonyloxy, halogen, optionally protected hydroxy, lower alkoxy, acyloxy or a group —OC(═X)N($R_{10}$)$R_{11}$;

or $R_5$ together with $R_{6a}$ forms a group —OC(═X)N(R'$_{10}$)-attached with the nitrogen atom to the carbon atom carrying $R_{6a}$, whereby X represents oxygen or sulfur, $R_{10}$ and $R_{11}$ independently represent hydrogen or lower alkyl or together with the nitrogen atom form a five- or six-membered ring optionally containing a second heteroatom such as nitrogen or oxygen, and R'$_{10}$ is hydrogen or lower alkyl;

or $R_5$ together with $R_{8a}$ represents oxy, whereby $R_8$ represents hydroxy;

$R_6$ represents hydroxy, and $R_{6a}$ represents hydrogen or together with $R_5$ forms a group —OC(═X)N(R'$_{10}$)-as defined above;

or $R_6$ and $R_{6a}$ together represent oxo;

R'$_5$ represents optionally protected hydroxy, lower alkoxy or acyloxy and

R'$_6$ represents hydroxy;

or R'$_5$ and R'$_6$ together form the —OC(═O)O— group;

R"$_5$ represents hydroxy or lower alkoxy and R"$_6$ represents hydroxy;

or R"$_5$ and R"$_6$ together form the —OC(═O)O— group;

$R_7$ represents methoxy or hydroxy;

$R_8$ represents an optionally protected hydroxy group, acyloxy, imidazolylcarbonyloxy or alkoxycarbonyloxy and $R_{8a}$ represents hydrogen;

or $R_8$ represents hydroxy and $R_{8a}$ together with $R_5$ represents oxy;

or $R_8$ together with $R_{8a}$ represents oxo; and n represents 1 or 2;

in free form or salt form, hereinafter briefly named "the compounds of the invention".

$R_1$ and $R_2$ preferably are optionally protected hydroxy. $R_3$ preferably is ethyl or allyl, especially ethyl. $R_4$ preferably is together with $R_{4a}$ oxo. $R_5$ preferably is hydroxy or together with $R_{8a}$ represents oxy. R'$_5$ and R"$_5$ preferably are hydroxy. $R_8$ preferably is hydroxy or oxo. $R_6$ preferably is together with $R_{6a}$ oxo. $R_7$ preferably is methoxy. The symbol ═══ preferably represents a single bond. n preferably is 2. X preferably is oxygen. $R_{10}$ and $R_{11}$ preferably are hydrogen or methyl or together with the nitrogen atom 1-imidazolyl, they especially are methyl. R'$_{10}$ preferably is hydrogen or methyl.

Acyl and acyloxy preferably are alkylcarbonyl or, respectively, alkylcarbonyloxy of altogether 2 to 5 carbon atoms, preferably acetyl(oxy), or formyl(oxy) or benzoyl(oxy). Halogen preferably is chlorine or bromine, it especially is chlorine. Lower alkyl and lower alkoxy preferably are of 1 to 4 carbon atoms, they especially are methyl and, respectively, methoxy. Protected hydroxy preferably is hydroxy protected by a conventional hydroxy-protecting group, it preferably is hydroxy protected by tert-butoxycarbonyl or trialkylsilyl, especially tert-butyldimethylsilyl. Alkoxycarbonyloxy preferably is of altogether 2 to 5 carbon atoms, it especially is methoxycarbonyloxy.

A compound of the invention in free form may be converted into a salt form where such forms exist, e.g. an acid addition salt form, in conventional manner and vice-versa.

A subgroup of compounds of the invention (compounds $Ip_1$) is the compounds of formulae I to III as defined above, with the proviso that $R_2$ and $R_4$ are other than together the —OC(=O)O— group;

$R_4$ is other than protected hydroxy;

$R_5$ is other than alkoxycarbonyloxy, halogen, protected hydroxy, a group —OC(=X)N($R_{10}$)$R_{11}$ as defined above or together with $R_{6a}$ a group —OC(=X)N($R'_{10}$)— as defined above;

$R'_5$ is other than protected hydroxy; and $R_8$ is other than protected hydroxy or alkoxycarbonyloxy of altogether more than 2 carbon atoms.

A further subgroup of compounds of the invention (compounds $Ip_2$) is the compounds of formulae I to III as defined above, with the proviso that $R_4$, $R_5$ and $R'_5$ are other than protected hydroxy, and $R_8$ is other than alkoxycarbonyloxy of altogether more than 2 carbon atoms.

A further group of compounds of the invention is the compounds of formulae Iq to IIIq

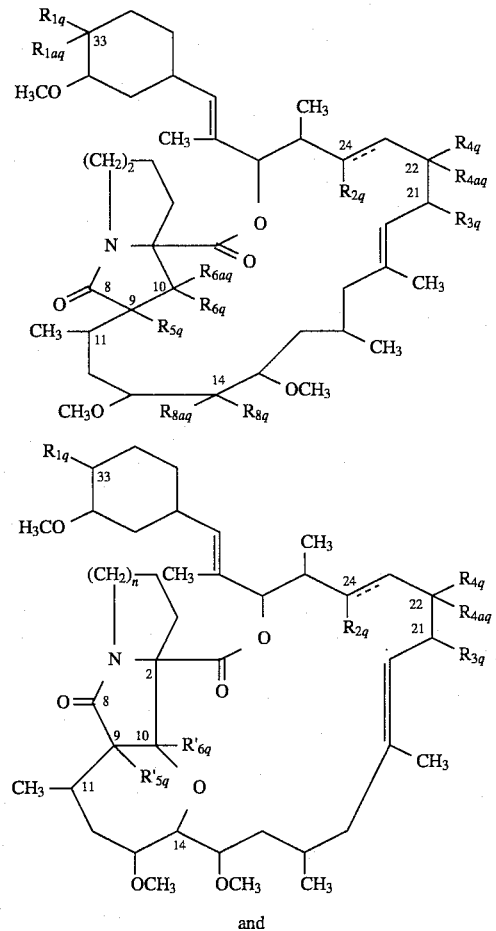

and

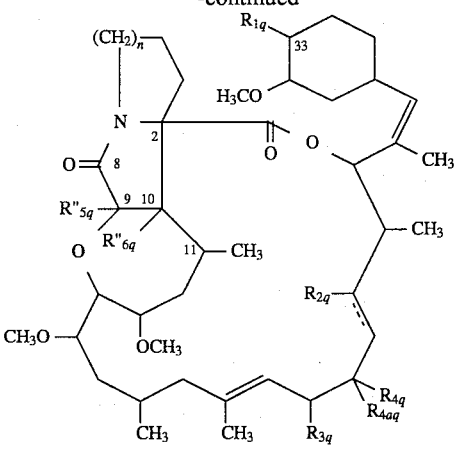

wherein $R_{1q}$ represents hydroxy optionally protected by tert-butyldimethylsilyl or methylsulfonyl and $R_{1aq}$ represents hydrogen; or $R_{1q}$ and $R_{1aq}$ together represent oxo;

$R_{2q}$ represents hydroxy optionally protected by tert-butyldimethylsilyl or together with $R_{4q}$ forms the —OC(=O)O— group;

$R_{3q}$ represents ethyl or allyl;

$R_{4q}$ represents hydroxy optionally protected by tert-butyldimethylsilyl or together with $R_{2q}$ forms the —OC(=O)O— group, and $R_{4aq}$ represents hydrogen;

or $R_{4q}$ together with $R_{4aq}$ represents oxo;

$R_{5q}$ represents methoxycarbonyloxy; chlorine; hydroxy optionally protected by tert-butyldimethylsilyl, tert-butoxycarbonyl or methylsulfonyl; methoxy; formyloxy, acetoxy or benzoyloxy; or a group —OC(=O)N($R_{10q}$)$R_{11q}$ wherein $R_{10q}$ and $R_{11q}$ independently represent hydrogen or methyl or together with the nitrogen atom form 4-morpholinyl;

or $R_{5q}$ together with $R_{6aq}$ forms a group —OC(=X)N($R'_{10q}$)— wherein X is as defined above and $R'_{10q}$ is hydrogen or methyl;

or $R_{5q}$ together with $R_{8aq}$ represents oxy, whereby $R_{8q}$ represents hydroxy;

$R_{6q}$ represents hydroxy, and $R_{6aq}$ represents hydrogen or together with $R_{5q}$ forms a group —OC(=X)N($R'_{10q}$)— as defined above;

or $R_{6q}$ and $R_{6aq}$ together represent oxo;

$R'_{5q}$ represents hydroxy optionally protected by benzoyl or acetyl and $R'_{6q}$ represents hydroxy;

or $R'_{5q}$ and $R'_{6q}$ together form the —OC(=O)O— group;

$R''_{5q}$ represents hydroxy or methoxy and $R''_{6q}$ represents hydroxy; or $R''_{5q}$ and $R''_{6q}$ together form the —OC(=O)O— group; and $R_{8q}$ represents hydroxy optionally protected by tert-butyldimethylsilyl or methylsulfonyl; acetoxy or benzoyloxy; or 1-imidazolylcarbonyloxy; and $R_{8aq}$ represents hydrogen;

or $R_{8q}$ represents hydroxy and $R_{8aq}$ together with $R_{5q}$ represents oxy;

or $R_{8q}$ together with $R_{8a}$ q represent oxo;

in free form or salt form.

The preferred stereochemical configuration of the compounds of formulae Iq to IIIq is as indicated below for formulae Is to Vs.

The invention also provides a process for the preparation of the compounds of formulae I to III, which comprises a) for the production of compounds of formulae

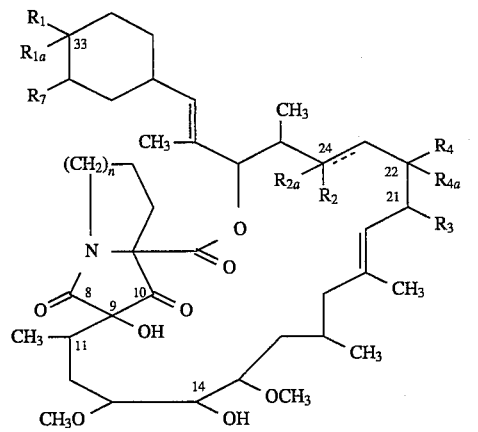

Ia

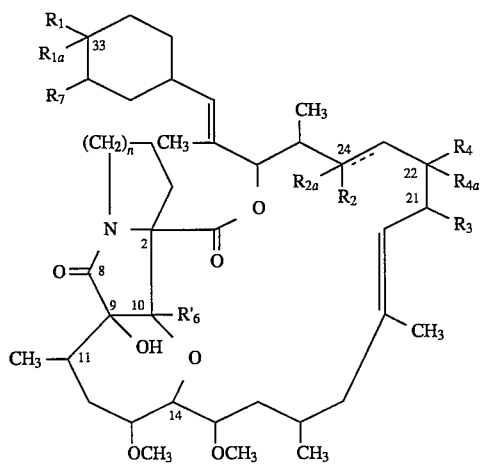

IIa and

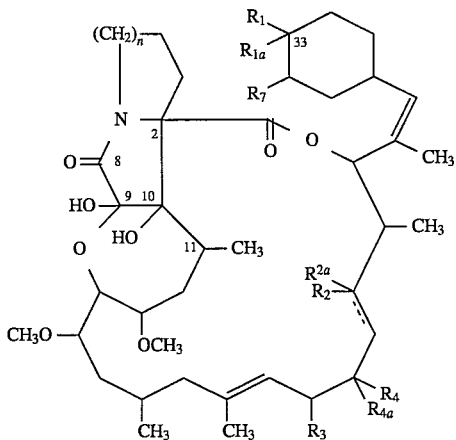

IIIa wherein the substituents are as defined above, reacting a compound of formula IV

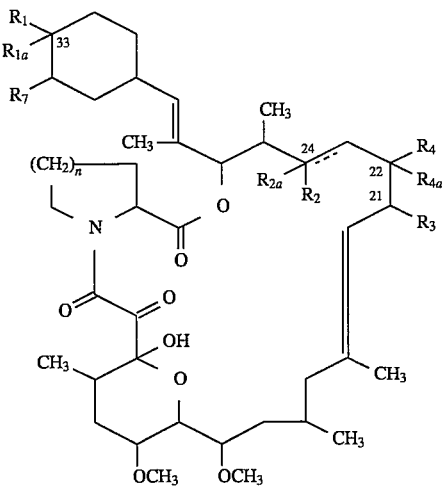

IV wherein the substituents are as defined above, with an appropriate base or organic or inorganic salt, optionally in the presence of a phase transfer catalyst, or b) for the production of compounds of formula Ia or IIa, reacting a compound of formula V

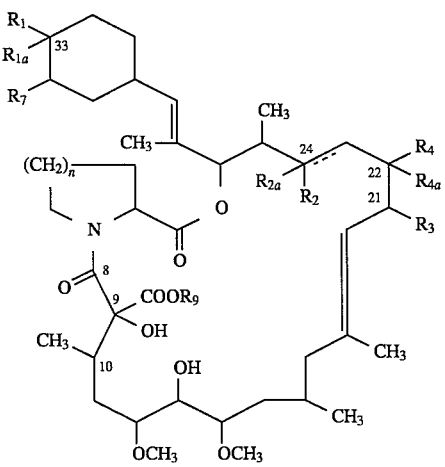

V wherein $R_9$ represents alkyl and the other substituents are as defined above, with an appropriate base or organic or inorganic salt, optionally in the presence of a phase transfer catalyst, or c) for the production of compounds of formulae I to III wherein $R_2$ and $R_4$, and/or $R'_5$ and $R'_6$ respectively $R''_5$ and $R''_6$ together form the —OC(=O)O— group, reacting a compound of formula I, II or III wherein $R_2$ and $R_4$, and/or $R'_5$ and $R'_6$ respectively $R''_5$ and $R''_6$ represent hydroxy, with phosgene, diphosgene or triphosgene in the presence of an acid binder, or d) for the production of compounds of formulae I to III wherein at least one of the substituents $R_1$, $R_2$, $R_4$, $R_6$ or $R_8$ represents hydroxy, appropriately reducing a compound of formula I, II or III wherein at least one of the substituents $R_1$, $R_2$, $R_4$, $R_6$ or $R_8$ together with $R_{1a}$, $R_{2a}$, $R_6$ a or, respectively, $R_{8a}$ represents oxo, or e) for the production of compounds of formulae I to III wherein $R_5$, $R'_5$ and $R''_5$ represent lower alkoxy, appropriately alkylating a compound of formula I, II or III wherein $R_5$, $R''_5$ and $R'_5$ represent hydroxy, or f) for the production of compounds of formula I or II wherein at least one of the substituents $R_5$, $R'_5$ or $R_8$ represents acyloxy, alkoxycarbonyloxy or —OC(=X)N($R_{10}$)$R_{11}$, appropriately acylating a compound of formula I or II wherein at least one of the substituents $R_5$, $R'_5$ or $R_8$ represents hydroxy, where indicated followed by the addition of $NH_3$ or of an appropriate amine, or g) for the production of compounds of formula I wherein $R_8$ together with $R_{8a}$ represents oxo, appropriately oxidizing a compound of formula I wherein $R_8$ represents hydroxy and $R_{8a}$ represents hydrogen, or h) for the production of compounds of formula I wherein $R_5$ represents halogen, appropriately halogenating a compound of formula I wherein $R_5$ represents hydroxy, and/or optionally deprotecting the resultant compounds of formulae I to III wherein a protected hydroxy group(s) is (are) present, and/or optionally protecting the resultant compounds of formulae I to III wherein a free hydroxy group(s) is (are) present, and recovering the resultant compounds in free form or salt form.

The process of the invention can be carried out in conventional manner.

In process variant a) and b) the reaction preferably is effected in an inert solvent, such as an ether, e.g. tetrahydrofuran, dioxane or diethylether, an aromatic hydrocarbon, e.g. benzene or toluene, an alcohol, e.g. methanol or ethanol, dimethylsulfoxide or acetonitrile. The bases or metallic salts are preferably CsF, $Cs_2CO_3$, $K_2CO_3$, LiOH, NaOH, KOH, $Mg(OR)_2$, whereby R represents a lower alkyl group, KH, NaH, a tertiary amine, e.g. triethylamine, or an amidine, e.g. 1,8-diazabicyclo[5.4.0]-undec-7-ene (DBU). As phase transfer catalyst quaternated ammonium salts or preferably crown ethers, e.g. crown [18.6], may be used. The reaction is preferably carried out at a temperature between about –30° and about 50° C., especially at about room temperature. Depending on the reaction conditions used (reactants, temperature, reaction time, etc.), specific regio- and/or diastereoisomeric forms of the compounds of formula Ia, IIa or IIIa or mixtures thereof are obtained.

In process variant b) the configuration in position 9 is determined by the configuration at position 9 in the starting material of formula V. Reaction mixtures may be worked up in conventional manner, e.g. chromatographically.

Process variant c) for the production of the carbonates is carried out preferably in an inert solvent such as an ether, e.g. tetrahydrofuran, diethylether or dioxane, a chlorinated hydrocarbon, e.g. 1,2-dichloroethane or methylene chloride, or acetonitrile, at temperatures between about –20° C. and the boiling temperature of the reaction mixture, preferably at about room temperature. A tertiary amine can be used as acid binder, e.g. triethylamine, 4-dimethylaminopyridine or pyridine.

The reduction, process variant d), can be effected in conventional manner. The reducing agent conveniently is a hydride-reagent, e.g. $NaBH_4$, diisobutyl aluminiumhydride or tetramethylammonium triacetoxy borohydride. The process may be carried out in an inert solvent such as an ether or cyclic ether, e.g. tetrahydrofuran, dioxane or diethylether, an aromatic hydrocarbon, e.g. toluene, or in the case of tetramethylammonium triacetoxy borohydride as reducing agent, also in acetonitrile and/or acetic acid, at temperatures preferably between about –70° and about 50° C., especially at about room temperature.

Process variant e) is an alkylation. It preferably is carried out in a non-protic solvent, e.g. in an ether, a cyclic ether, an aromatic hydrocarbon, dimethyl formamide or dimethyl sulfoxide, in the presence of a base such as a non-nucleophilic nitrogen base, e.g. DBU, or an alkali hydride, e.g. sodium or potassium hydride, or a metallic salt, e.g. a carbonate or fluoride of potassium, sodium or cesium, optionally in the presence of a crown ether. The alkylating agent preferably is a halogenide, tosylate or mesylate, e.g. alkyl iodide, especially methyl iodide. The reaction is carried out at room temperature or elevated temperature, preferably at room temperature.

Acylation according to process variant f) can be carried out in conventional manner, e.g. in an inert solvent such as acetonitrile or dichloromethane, e.g. with an acid chloride or an acid anhydride in the presence of an acid binder such as 4-dimethylaminopyridine or with an acid in the presence of 4-dimethylaminopyridine or with an acid in the presence of a carbodiimide such as dicyclohexylcarbodiimide. The acylation may be carried out with diphosgene or thiophosgene followed by the addition of $NH_3$ or of an appropriate amine to give the corresponding carbamates wherein $R_5$ represents a group of formula —OC(=X)N($R_{10}$)$R_{11}$ as defined above. When the reaction is carried out in the presence of $NH_3$ or a primary amine, the end products wherein $R_6$ and $R_{6a}$ together represent oxo may undergo a cyclisation and form compounds of formula

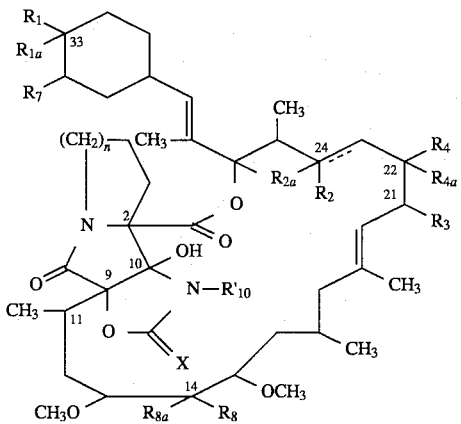

Ib wherein the substituents are as defined above and which also form part of the invention.

Process variant g) is an oxidation. It may be carried out in conventional manner, e.g. in an inert solvent such as an aromatic hydrocarbon, e.g toluene, or a halogenated hydrocarbon, e.g. dichloromethane or dichloroethane, at temperatures between about 0° C. and room temperature, preferably at about room temperature. The reaction is effected e.g. with N-methyl-morpholine-N-oxide in the presence of a catalytic amount of tetrapropylammonium perruthenate, or with 1,1, 1-tris(acetoxy)-1,1-dihydrobenziodoxol-3(1H)one (Dess-Martin method). The oxidized end compounds of formula I wherein $R_8$ together with $R_{8a}$ represents oxo and $R_5$ represents hydroxy, may exist in equilibrium with corresponding compounds of formula I wherein $R_8$ represents hydroxy and $R_5$ together with $R_{8a}$ represents oxy, i.e. with compounds of formula Ic

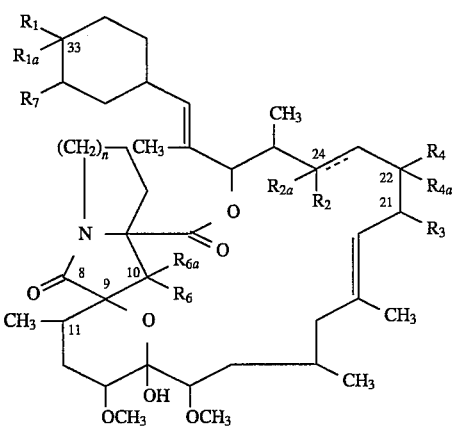

Ic wherein the substituents are as defined above and which also form part of the invention. Process variant g) gives mixtures of these compounds which may be separated in conventional manner, e.g. chromatographically. Depending on the starting material and the reaction conditions employed, especially on the oxydizing reagent, the oxydation may take place in the positions 10, 14, 22, 24 and/or 33. Different reaction ability and/or selective protection of hydroxy groups may yield final products which are oxydized only in selected positions.

Process variant h) may be carried out in for halogenation conventional manner, e.g. by reacting with a halogenating agent such as thionyl chloride in an appropriate solvent, e.g. in pyridine or tetrahydrofuran, at temperatures e.g. between about 0° C. and room temperature, preferably at about room temperature.

The process variants of the invention may be carried out simultaneously, especially process variant e) may be effected in a "one pot reaction" with process variants a) or b). Mixtures of end products may be separated in conventional manner, e.g. chromatographically.

Compounds of formula Ia may be in equilibrium with compounds of formula IIa. In many cases these tautomeric forms may be isolated.

Process variants a) and b) signify generally a) when reacting a compound of formula IV to obtain compounds of formulae Ia and IIa: rearrangement and cyclisation;

b) when reacting a compound of formula IV to obtain compounds of formula IIIa: cyclisation;

c) when reacting a compound of formula V to obtain compounds of formulae Ia and IIa: cyclisation.

When compounds obtained according to process variants a) to h) have one or more protected hydroxy group(s), the protecting group(s) may be removed in conventional manner to give the corresponding unprotected compounds. The removal of e.g. tert-butyldimethylsilyl or tert-butoxycarbonyl may be effected by treatment with hydrofluoric acid in a solvent such as acetonitrile. Depending on the reaction conditions chosen (e.g. duration or temperature) the removal can be steered in such a manner that either all or only some protecting groups are eliminated.

When compounds obtained according to process variants a) to h) have one or more free hydroxy group(s), the hydroxy group(s) may be protected in conventional manner to give the corresponding protected compounds. Depending on the reaction conditions chosen the reaction can be steered in such a manner that either all or only some hydroxy groups are protected. Suitable protecting groups are conventional hydroxy protecting groups such as tert-butoxycarbonyl or trialkylsilyl, preferably tert-butyldimethylsilyl.

Partial deprotection or protection is particularly indicated where a definite hydroxy group is to be reacted in a subsequent reaction step.

The compounds of formulae I to V have a number of chiral centers and may exist in a variety of stereoisomers. The process variants of the invention result normally in a mixture of such isomers. Depending on the conditions and the type of reaction the process can be steered in such manner that a specific isomer preferably is produced. The invention provides all optical and geometric isomers as well as racemic mixtures. The isomers may be resolved or separated by conventional techniques. However the preferred stereochemistry at various chiral carbon atoms is shown in formulae Is to Vs:

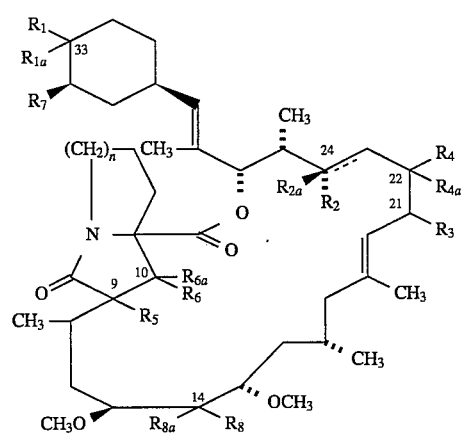

Is

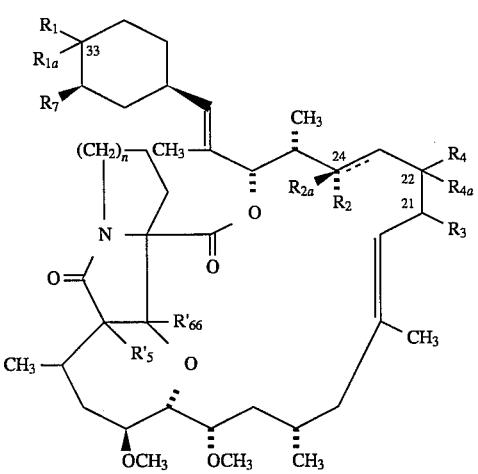

IIs

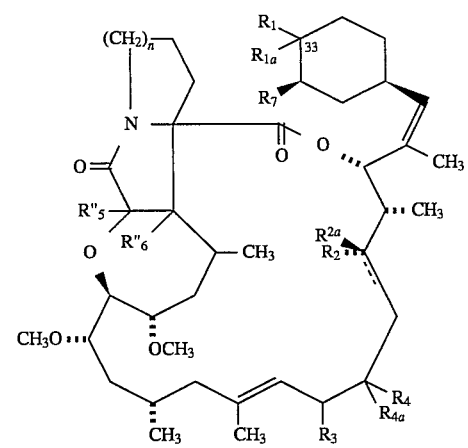

IIIs

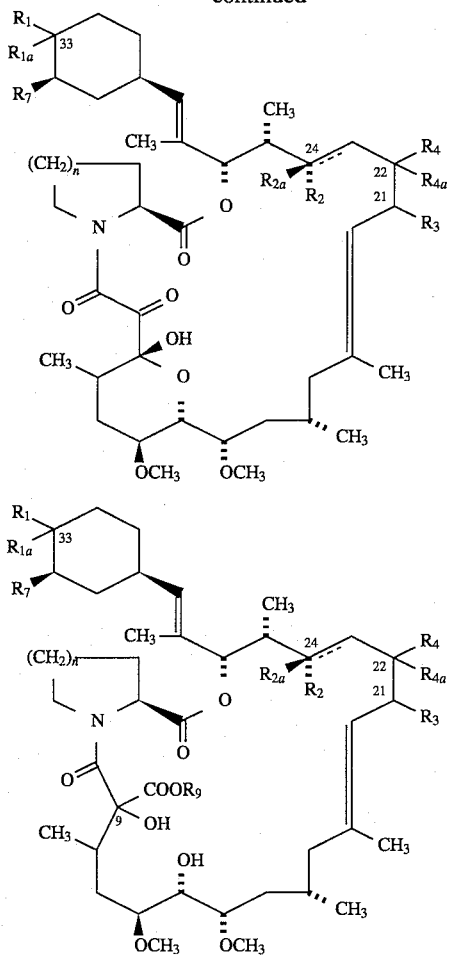

In the above formulae Is to Vs when $R_1$ is other than oxo together with $R_{1a}$, then $R_1$ preferably is bound with the α-configuration to the carbon atom in 33 position;

$R_3$ preferably is bound with the α-configuration to the carbon atom in 21 position;

when $R_4$ is other than oxo together with $R_{4a}$, then $R_4$ preferably is bound with the α-configuration to the carbon atom in 22 position;

A compound of the invention may be isolated and purified from the reaction mixture in conventional manner.

The starting material of formula V, preferably in form of the diastereoisomers hereinafter designated diastereoisomers C, may be obtained by reacting a compound of formula IV analogously to process variant a) followed by reaction of the resultant product with a diazoalkane. The first step of this process may be carried out as described above, e.g. with KOH/crown ether in tetrahydrofuran. The reaction product is worked up in conventional manner, the residue redissolved in an inert solvent, e.g. dichloromethane, and triturated with a solution of a diazoalkane, preferably diazomethane or diazoethane, in an inert solvent, e.g. ether. The resultant reaction mixture may be worked up in conventional manner.

The starting material of formula V, preferably in form of the diastereoisomers hereinafter designated diastereoisomers A, may be obtained by reacting a compound of formula IV with a base, followed by reaction of the resultant product with a diazoalkane. This process step may be carried out in conventional manner. It preferably is effected in a mixture of solvents, e.g. in a mixture of tetrahydrofuran and water, using LiOH or Ca(OH)$_2$ as base. The reaction product is worked up in conventional manner, the residue redissolved in an inert solvent, e.g. dichloromethane, and titurated with a solution of a diazoalkane, preferably diazomethane or diazoethane, in an inert solvent, e.g. ether. The resultant reaction mixture may be worked up in conventional manner.

Insofar as their preparation is not specifically described herein, e.g. in the Examples, the compounds used as starting materials are known or can be obtained in conventional manner from known compounds, e.g. starting from appropriate Streptomyces strains such as Streptomyces tsukubaensis No. 9993 described in e.g. Fujisawa EP 184162. Samples can be obtained from the Fermentation Research Institute, Tsukuba, Ibaraki 305, Japan under provisions of the Budapest Treaty under deposit No. FERM BP-927. This strain has been redeposited on Apr. 27, 1989 with the Agricultural Research Culture Collection International Depository, Peoria, Ill. 61604, USA under the provisions of the Budapest Treaty under deposit No. NRRL 18488.

The following Examples illustrate the invention. They are not limitative. All temperatures are in degrees Centigrade. In the NMR spectra all chemical shift values are in ppm; samples are measured in CDCl$_3$ unless indicated otherwise. The following abbreviations are used:

O-tBDMS=tert-butyldimethylsilyloxy
db=double bond
sb=single bond
Im=1-imidazolylcarbonyl
Bz=benzoyl
DBU=1,8-diazabicyclo[5.4.0]undec-7-ene
Ac=acetyl
BOC=tert-butoxycarbonyl

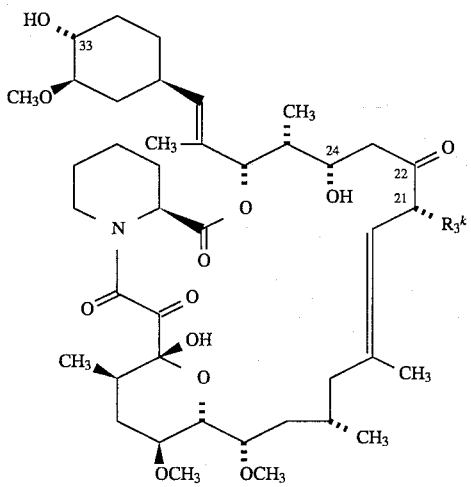

Formula Ik ($R_3^k$ = allyl) = FK 506;

Formula Ik ($R_3^k$ = ethyl) = FR 520.

EXAMPLE 1

$R_1=R_2$=O-tBDMS; $R_3=C_2H_5$; $R_{4a}$=O; $R_7$=OCH$_3$;
≡≡=sb; n=2; $R_{1a}=R_{2a}$=H (process a)

1a: compound of formula IIIa
1b: compound of formula IIa (diastereoisomer A)
1c: compound of formula Ia (diastereoisomer A)
1d: compound of formula Ia (diastereoisomer B)
1e: compound of formula Ia (diastereoisomer C)

4 g of crown[18.6]ether and 12.7 g of cesium carbonate (or 5 g of cesium fluoride) are added to a solution of 20 g 24,33-bis-O-tBDMS-FR 520 in 250 ml of dry tetrahydrofuran. The reaction mixture is stirred for 3 hours at room temperature, then partitioned between ethyl acetate and 1N hydrochloric acid, the phases are separated, the organic phase is washed with brine, dried over sodium sulfate, filtered and evaporated under vacuum. Chromatography of the residue (n-hexane/ethyl acetate=3/1→1/2) gives the title substances as colourless foams.

EXAMPLE 2

$R_1=R_2=$O-tBDMS; $R_3=C_2H_5$; $R_4+R_{4a}=$O; $R_7=$OCH$_3$; ═══=sb; n=2; $R_{1a}=R_{2a}=$H; diastereoisomers A (process b)
2a: compound of formula IIa
2b: compound of formula Ia 1 ml of diazabicycloundecene is added to a solution of 5.2 g of the compound of formula V ($R_1=R_2=$O-tBDMS; $R_{1a}=R_{2a}=$H; $R_3=C_2H_5$; $R_4+R_{4a}=$O; $R_7=$OCH$_3$; $R_9=$CH$_3$; n=2; +e,ovs ─ ─ ─$_{+ee}$ =sb; diastereoisomer A) in 250 ml of acetonitrile. The reaction mixture is stirred for 70 minutes at room temperature and then worked up as described in example 1 (n-hexane/ethyl acetate=3/2) to give the title substances as colourless foams.

Analogously as described in examples 1 and 2 the following compounds of formulae Ia, IIa and IIIa are obtained in form of colourless foams ($R_7=$OCH$_3$; n=2; +e,ovs ─ ─ ─$_{+ee}$ =sb; $R_{1a}=R_{2a}=$H):

To a solution of 0.8 g of the compound of formula III ($R_1=R_2=$ O-tBDMS; $R_3=C_2H_5$; $R_4+R_{4a}=$O; $R''_5=R''_6=$OH; $R_7=$OCH$_3$; ═══=sb; n=2; $R_{1a}=R_{2a}=$H) in 40 ml of acetonitrile are added in turn 0.2 ml of diphosgene and 1.75 g of dimethylaminopyridine. The reaction mixture is stirred for 1.5 hours at room temperature and then worked up as described in example 1 (n-hexane/ethyl acetate=9/1) to give the title substance in form of a colourless foam.

Analogously as described in example 13 the following compounds of formulae I to III are obtained in form of colourless foams ($R_3=C_2H_5$; $R_7=$OCH$_3$; ═══=sb; n=2; $R_{1a}=R_{2a}=R_{4a}=R_{8a}=$H):

| ex: | form. | isomer | $R_1$ | $R_2$ | $R_4$ | $R_{4a}$ | $R_3$ | starting material: |
|---|---|---|---|---|---|---|---|---|
| 3a | IIIa | — | —O—tBDMS | —O—tBDMS | O | | —CH$_2$CH═CH$_2$ | 24,33-di—O—tBDMS—FK 506 |
| 3b | IIa | A | —O—tBDMS | —O—tBDMS | O | | —CH$_2$CH═CH$_2$ | |
| 3c | Ia | A | —O—tBDMS | —O—tBDMS | O | | —CH$_2$CH═CH$_2$ | |
| 3d | Ia | C | —O—tBDMS | —O—tBDMS | O | | —CH$_2$CH═CH$_2$ | |
| 4 | IIIa | — | —O—SO$_2$—CH$_3$ | —O—tBDMS | O | | —C$_2$H$_5$ | Compound A) |
| 5 | IIIa | — | —O—SO$_2$—CH$_3$ | —O—tBDMS | O | | —CH$_2$CH═CH$_2$ | Compound B) |
| 6a | IIIa | — | —OH | —OH | O | | —C$_2$H$_5$ | FR 520 |
| 6b | IIa | A | —OH | —OH | O | | —C$_2$H$_5$ | |
| 6c | Ia | A | —OH | —OH | O | | —C$_2$H$_5$ | |
| 6d | Ia | B | —OH | —OH | O | | —C$_2$H$_5$ | |
| 6e | Ia | C | —OH | —OH | O | | —C$_2$H$_5$ | |
| 6f | Ia | D | —OH | —OH | O | | —C$_2$H$_5$ | |
| 7a | IIIa | — | —OH | —OH | O | | —CH$_2$CH═CH$_2$ | FK 506 |
| 7b | IIa | A | —OH | —OH | O | | —CH$_2$CH═CH$_2$ | |
| 7c | Ia | A | —OH | —OH | O | | —CH$_2$CH═CH$_2$ | |
| 7d | Ia | B | —OH | —OH | O | | —CH$_2$CH═CH$_2$ | |
| 7e | Ia | C | —OH | —OH | O | | —CH$_2$CH═CH$_2$ | |
| 8 | Ia | A | —O—tBDMS | —OH | O | | —C$_2$H$_5$ | 33-O—tBDMS-FR520 a) |
| 9a | IIIa | — | —O—tBDMS | —O—CO—O— | | H | —C$_2$H$_5$ | Compound G) |
| 9b | Ia | A | —O—tBDMS | —O—CO—O— | | H | —C$_2$H$_5$ | |
| 9c | Ia | C | —O—tBDMS | —O—CO-O— | | H | —C$_2$H$_5$ | |
| 10 | Ia | C | —O—tBDMS | —O—tBDMS | O | | —C$_2$H$_5$ | Compound C) |
| 11 | Ia | C | —O—tBDMS | —O—tBDMS | O | | —CH$_2$CH═CH$_2$ | Compound D) |
| 12a | Ia | A | —O—tBDMS | —O—tBDMS | O | | —CH$_2$CH═CH$_2$ | Compound F) |
| 12b | IIa | A | —O—tBDMS | —O—tBDMS | O | | —CH$_2$CH═CH$_2$ | | a) Deprotection or, respectively, reduction of this compound gives the compound of Example 6c (= Example 73) or, respectively, of Example 28

EXAMPLE 13

Compound of formula III ($R_1=R_2=$O-tBDMS; $R_3=C_2H_5$; $R_4+R_{4a}=$O; $R''_5+R''_6=$OCO—O; $R_7=$OCH$_3$; ═══=sb; n=2; $R_{1a}=R_{2a}=$H (process c)

| ex: | form. | isomer | $R_1$ | $R_2$ | $R_4$ | $R_5$ $R'_5$ $R''_5$ | $R_6$ $R'_6$ $R''_6$ | $R_8$ | starting material: |
|---|---|---|---|---|---|---|---|---|---|
| 14 | II | A | —O—tBDMS | —O—tBDMS | —O—tBDMS | —O—CO—O— | — | — | Ex. 1b |
| 15 | I | A | —O—tBDMS | —O—CO—O— | | OH | O* | OH | Ex. 28 |
| 16 | I | C | —OH | —O—CO—O— | | —O—BOC | O* | OH | Ex. 27 |
| 17 | III | — | —OH | —O—CO—O— | | —O—CO—O— | — | — | Ex. 25 |
| 18 | I | B | —OH | —O—CO—O— | | OH | O* | OH | Ex. 26a |

*together with $R_{6a}$

EXAMPLE 19

Compound of formula I ($R_1=R_2$=O-tBDMS; $R_3=C_2H_5$; $R_4+R_{4a}$=O; $R_5=R_6=R_8$=OH; $R_7$=OCH$_3$; ⎓=sb; n=2; $R_{1a}=R_{2a}=R_{6a}=R_{8a}$=H; diastereoisomer C) (process d)

0.5 g of tetramethylammonium triacetoxy boronhydride are added to a solution of 1 g of the compound of formula I ($R_1=R_2$=O-tBDMS; $R_3=C_2H_5$; $R_{1a}=R_{2a}=R_{8a}$=H; $R_4+R_{4a}$=$R_6+R_{6a}$=O; $R_5=R_8$=OH; $R_7$=OCH$_3$; ⎓=sb; diastereoisomer C) in 30 ml of acetonitrile and 5 ml of acetic acid. The reaction mixture is stirred for 3.5 hours at room temperature and then partitioned between saturated aqueous NaHCO$_3$-solution and ethyl acetate. The organic phase is separted, washed in turn with brine, 1N hydrochloric acid and brine again, dried over Na$_2$SO$_4$, filtered and evaporated under vacuum. Chromatography of the residue (ethyl acetate) gives the title substance in form of a colourless foam.

Analogously as described in example 19 the following compounds of formulae I, II and III are obtained in form of colourless foams ($R_3=C_2H_5$; $R_7$=OCH$_3$; $R_8$=OH; $R_{1a}=R_{2a}$=H; ⎓=sb; n=2):

200 mg of crown [18.6]ether, 200 mg of cesium carbonate and 1.5 ml of methyl iodide are added to a solution of 100 mg of the compound of formula I ($R_1=R_2$=O-tBDMS; $R_3=C_2H_5$; $R_{1a}=R_{2a}=R_{8a}$=H; $R_4+R_{4a}$=$R_6+R_{6a}$=O; $R_5=R_8$=OH; $R_7$=OCH$_3$; ⎓=sb; n=2; diastereoisomer A) and stirred for 1.5 hours at room temperature. The reaction mixture is worked up as described in example 1 (n-hexane/ethyl acetate=2/1) to give the title substance in form of a colourless foam.

Analogously as described in example 29 the following compounds of formula I and III are obtained in form of colourless foams ($R_3=C_2H_5$; $R_{1a}=R_{2a}=R_{8a}$=H; $R_4+R_{4a}$=O; $R_7$=OCH$_3$; $R_8$=OH; ⎓=sb; n=2):

| ex: | form. | isomer | $R_1$ | $R_2$ | $R_5$ | $R''_6$ $R_6$ | $R_{6a}$ | starting material |
|---|---|---|---|---|---|---|---|---|
| 30 | III | — | —O—tBDMS | —O—tBDMS | —OCH$_3$ | OH | — | Ex. 1a |
| 31 | I | C | —O—tBDMS | —O—tBDMS | —OCH$_3$ | O | | Ex. 1e |

EXAMPLE 32

$R_1=R_2$=O-tDMS; $R_3=C_2H_5$; $R_4+R_{4a}$=O; $R_7$=OCH$_3$; ⎓=sb; n=2; $R_{1a}=R_{2a}$=H; diastereoisomer A (process f)

32a: compound of formula I ($R_5$=OH; $R_6+R_{6a}$=O; $R_8$=O-Bz; $R_{8a}$=H)

32b: compound of formula I ($R_5$=O-Bz; $R_6+R_{6a}$=O; $R_8$=O-Bz; $R_{8a}$=H)

32c: compound of formula I ($R_5$=O-Bz; $R_6+R_{6a}$=O; $R_8$=OH; $R_{8a}$=H)

32d: compound of formula II: ($R'_5$=O-Bz; $R'_6$=OH)

| ex: | form. | isomer | $R_1$ | $R_2$ | $R_4$ | $R_{4a}$ | $R_5$ $R'_5$ $R''_5$ | $R_6$ $R'_6$ $R''_6$ | $R_{6a}$ | starting material |
|---|---|---|---|---|---|---|---|---|---|---|
| 20 | I | B | —O—tBDMS | —O—tBDMS | O | | OH | OH | H | Ex. 1d |
| 21 | I | A | —O—tBDMS | —O—tBDMS | O | | OH | OH | H | Ex. 1c |
| 22 | II | A | —O—tBDMS | —O—tBDMS | OH | H | OH | OH | — | Ex. 1b |
| 23a | I | A/cis | OH | —O—CO—O— | | H | OH | OH | H | Ex. 112 |
| 23b | I | A/trans | OH | —O—CO—O— | | H | OH | OH | H | |
| 24a | I | C | —O—tBDMS | —O—tBDMS | OH | H | OH | | O | Ex. 1e a) |
| 24b | I | C | —O—tBDMS | —O—tBDMS | OH | H | OH | OH | H | |
| 25 | III | — | —O—tBDMs | —O—tBDMS | OH | H | —O—CO—O— | | — | Ex. 100 |
| 26a | I | B | OH | OH | H | | OH | | O | Ex. 6d |
| 26b | I | B | OH | OH | H | | OH | OH | H | |
| 27 | I | C | OH | OH | OH | H | O—BOC | | O | Ex. 115 |
| 28 | I | A | —O—tBDMS | OH | OH | H | OH | | O | Ex. 8 | a) Deprotection gives the compound of Example 118

EXAMPLE 29

Compound of formula I ($R_1=R_2$=O-tBDMS; $R_3=C_2H_5$; $R_4+R_{4a}$=$R_6+R_{6a}$=O; $R_5=R_7$=OCH$_3$; $R_8$=OH; ⎓=sb; n=2; $R_{1a}=R_{2a}=R_{8a}$=H) (process d)

5 mol equivalents of 4-dimethylaminopyridine and 1.3 mol equivalents of benzoyl chloride are added to a solution of 0.6 g of the compound of formula I ($R_1=R_2=$O-tBDMS; $R_3=C_2H_5$; $R_{1a}=R_{2a}=R_{8a}=$H; $R_4+R_{4a}=R_6+R_{6a}=$O; $R_5=R_8=$OH; $R_7=$OCH$_3$; diastereoisomer A) or of the compound of formula II ($R_1=R_2=$O-tBDMS; $R_3=C_2H_5$; $R_{1a}=R_{2a}=$H; $R_4+R_{4a}=$O; $R'_5=$OH; $R'_6=$OH; $R_7=$OCH$_3$; ====sb; n=2). The reaction mixture is stirred for 45 minutes and then worked up as described in example 1 (n-hexane/ethyl acetate=4/1→2/1) to yield the title substances in form of colourless foams.

Analogously as described in example 32 the following compounds of formula I and II are obtained in form of colourless foams ($R_1=R_2=$O-tBDMS; $R_3=C_2H_5$; $R_{1a}=R_{2a}=$H; $R_4+R_{4a}=$O; $R_7=$OCH$_3$; ====sb; n=2):

$R_7=$OCH$_3$; ====sb; n=2; $R_6=$OH; $R_{1a}=R_{2a}=R_{6a}=$H):

| ex: | form. | isomer | $R_5$ | $R_6$ $R'_6$ | $R_{6a}$ | $R_8$ | $R_{8a}$ | starting material |
|---|---|---|---|---|---|---|---|---|
| 33 | I | A | OH | O | | O—Im | H | Ex. 1b or 1c |
| 34 | I | C | O—Ac | O | | O—Ac | H | Ex. 1e |
| 35a | I | C | O—Bz | O | | O—Bz | H | } Ex. 1e |
| 35b | I | C | O—Bz | O | | OH | H | |
| 36a | I | C | —O—SO$^2$CH$_3$ | O | | —O—SO$^2$CH$_3$ | H | } Ex. 1e |
| 36b | I | C | OH | O | | —O—SO$_2$CH$_3$ | H | |
| 37a | I | A | O—Ac | O | | O—Ac | H | |
| 37b | I | A | OH | O | | O—Ac | H | } Ex. 1b or 1c |
| 37c | I | A | O—Ac | O | | OH | H | |
| 37d | II | A | O—Ac | OH | — | — | — | |
| 38 | I | A | —O—CHO | O | | O | | Ex. 50 |
| 39 | I | A | —O—COOCH$_3$ | O | | —OtBDMS | H | Ex. 58b |
| 40 | I | A | —O—CHO | O | | —OtBDMS | H | Ex. 58b a) |
| 41 | I | B | —O—CHO | O | | —OtBDMS | H | Ex. 60a |
| 42 | I | C | —O—CHO | O | | —OtBDMS | H | Ex. 59 |
| 43 | I | C | —O—BOC | O | | —OtBDMS | H | Ex. 59 | a) Deprotection gives the compound of Example 6c (= Example 73)

EXAMPLE 44

Compound of formula I ($R_1=R_2=R_8=$0-tBDMS; $R_3=C_2H_5$; $R_4+R_{4a}=R_6+R_{6a}=$O; $R_5=$O—CO—(4-morpholinyl); $R_7=$OCH$_3$; ====sb; n=2; $R_{1a}=R_{2a}=R_{8a}=$H; diastereoisomer A) (process f)

10 equ. of 4-dimethylaminopyridine and 1 molequ. of diphosgene are added to a solution of 2 g of the compound

| ex. | form. | isomer | $R_5$ | $R_8$ | $R_{8a}$ | starting material | |
|---|---|---|---|---|---|---|---|
| 45 | I | A | —O—CO—NH$_2$ | —O—tBDMS | H | Ex. 58b | |
| 46 | I | A | —O—CO—N(CH$_3$)$_2$ | —O—tBDMS | H | Ex. 58b | |
| 47a | Ib | C | — | O | | } ($R'_{10}$ = H, X = O) | Ex. 51 |
| 47b | I | C | —O—CO—NH$_2$ | O | | | |
| 48 | Ib | A | — | —O—tBDMS | H | ($R'_{10}$ = CH$_3$, X = O) | } Ex. 58b |
| 49 | Ib | A | — | —O—tBDMS | H | ($R'_{10}$ = CH$_3$, X = S) | | of formula I ($R_1=R_2=R_8=$ O-tBDMS; $R_3C_2H_5$; $R_{1a}=R_{2a}=R_{8a}=$H; $R_4+R_{4a}=R_6+R_{6a}=$O; $R_5=$OH; $R_7=$OCH$_3$; ====sb; n=2; diastereoisomer A) in 50 ml of acetonitrile, the reaction mixture is stirred for 20 minutes at room temperature, then poured onto 500 ml of ethyl acetate and 20 ml of morpholine, rigorously stirred for 10 minutes and then worked up as described in example 1 (n-hexane/ethyl acetate=7/1) to yield the substance as a colourless foam.

Analogously as described in example 44 the following compounds of formula I and Ib are obtained in form of colourless foams ($R_1=R_2$O-tBDMS; $R_3=C_2H_5$; $R_4+R_{4a}=$O;

EXAMPLE 50

Compound of formula I ($R_1=R_2=$O-tBDMS; $R_3=C_2H_5$; $R_4+R_{4a}=R_6+R_{6a}=R_8+R_{8a}=$O; $R_5=$OH; $R_7=$OCH$_3$; ====sb; n=2; $R_{1a}=R_{2a}=$H; diastereoisomer A) (process g)

0.5 g of 1,1,1-tris(acetoxy)-1,1-dihydro-benziodoxol-3(1H)-one are added to a solution of 0.5 g of the compound of formula I ($R_1=R_2=$O-tBDMS; $R_3=C_2H_5$; $R_4+R_{4a}=R_{6a}=$O; $R_5=R_8=$OH; $R_7=$OCH$_3$; ====sb; n=2; $R_{1a}=R_{2a}=R_{8a}=$H;

diastereoisomer A) in 50 ml of methylene chloride. The reaction mixture is stirred for 3 hours at room temperature, then filtered over silicagel, washed with n-hexane/ethyl acetate (1/1) and the filtrate evaporated under vacuum. Chromatography of the residue (n-hexane/ethyl acetate=3/1) gives the title substance in form of a colourless foam.

Analogously as described in example 50 the following compounds of formula I are obtained in form of colourless foams ($R_3=C_2H_5$; $R_4+R_{4a}=R_6+R_{6a}=R_8+R_{8a}=O$; $R_7=OCH_3$; ===sb; n=2; $R_{2a}=H$):

| ex. | iso-mer | $R_1$ | $R_{1a}$ | $R_2$ | $R_5$ | starting material |
|---|---|---|---|---|---|---|
| 51 | C | —O—tBDMS | H | —O—tBDMS | OH | Ex. 1e |
| 52 | A | O | | —O—tBDMS | OH | Ex. 70 |
| 53 | A | —O—tBDMS | H | —O—tBDMS | $OCH_3$ | Ex. 29 |
| 54 | C | —O—tBDMS | H | —O—tBDMS | $OCH_3$ | Ex. 31 |

EXAMPLE 55

Compound of formula I ($R_1=R_2=R_8=O$-tBDMS; $R_3=C_2H_5$; $R_4+R_{4a}=R_6+R_{6a}=O$; $R_5=Cl$; $R_7=OCH_3$; ===sb; n=2; $R_{1a}=R_{2a}=R_{8a}=H$; diastereoisomer epi-A) (process h)

0.3 ml of thionyl chloride in 5 ml of pyridine are added to a solution of 1 g of the compound of formula I ($R_1=R_2=O$-tBDMS; $R_3=C_2H_5$; $R_4+R_{4a}=R_6+R_{6a}=O$; $R_5=OH$; $R_7=OCH_3$; $R_8=O$-t-BDMS; $R_{1a}=R_{2a}=R_{8a}=H$; ===sb; n=2; diastereoisomer A) in 100 ml of tetrahydrofuran, the reaction mixture is stirred at room temperature for 15 hours and then partitioned between ethyl acetate and a saturated aqueous solution of sodium bicarbonate. The organic phase is separated, washed twice with 1N HCl and water, dried over $Na_2SO_4$ and the solvents are removed under vacuo. Column chromatography (n-hexane/ethyl acetate=9/1) gives the title compound as a colourless foam.

Analogously as described in example 55 the following compounds of formula I are obtained in form of colourless foams ($R_3=C_2H_5$; $R_4+R_{4a}=R_6+R_{6a}=O$; $R_7=OCH_3$; $R_8=O$-tBDMS; $R_{1a}=R_{2a}=R_{8a}=H$; ===sb; n=2):

| ex: | isomer | $R_1$ | $R_2$ | $R_5$ | starting material |
|---|---|---|---|---|---|
| 56 | epi-C | —O—tBDMS | —O—tBDMS | Cl | Ex. 59 |
| 57 | epi-B | —O—tBDMS | —O—tBDMS | Cl | Ex. 60a |

EXAMPLE 58

Compound of formula I ($R_1=R_2=R_8=O$-tBDMS; $R_3=C_2H_5$; $R_4+R_{4a}=R_6+R_{6a}=O$; $R_7=OCH_3$; ===sb; n=2; $R_{1a}=R_{2a}=R_{8a}=H$; diastereoisomer A) (protection)

a) $R_5=O$-tBDMS
b) $R_5=OH$ 5 equ. of 2,6-lutidine and 2 equ. of t.butyldimethylsilyl triflate are added to a solution of the compound of formula I ($R_1=R_2=O$-tBDMS; $R_3=C_2H_5$; $R_4+R_{4a}=R_6+R_{6a}=O$; $R_5=R_8=OH$; $R_7=OCH_3$; $R_{1a}=R_{2a}=R_{8a}=H$; ===sb; n=2; diastereoisomer A) in 50 ml of acetonitrile, the reaction mixture is stirred for 1.5 hours at room temperature and then worked up as described in example 1. Chromatography (eluent=toluene) gives the title compounds as colourless foams.

Analogously as described in example 58 the following compounds of formula I are obtained in form of colourless foams ($R_1=R_2=R_8=O$-tBDMS; $R_3=C_2H_5$; $R_4+R_{4a}=R_6+R_{6a}=O$; $R_7=OCH_3$; ===sb; n=2;

| ex: | isomer | $R_5$ | starting material: |
|---|---|---|---|
| 59 | C | OH | Ex. 1e |
| 60a | B | OH | Ex. 1d |
| 60b | B | —O—tBDMS | Ex. 1d |

EXAMPLE 61

Compound of formula III ($R_1=OH$; $R_2=O$-tBDMS; $R_3=C_2H_5$; $R_4+R_{4a}=O$; $R''_5=R''_6=OH$; $R_7=OCH_3$; ===sb; n=2; $R_{1a}=R_{2a}=H$) (partial deprotection)

3 ml of 40% aqueous hydrofluoric acid are added to a solution of 0.5 g of the compound of formula III ($R_1=R_2=O$-tBDMS; $R_3=C_2H_5$; $R_4+R_{4a}=O$; $R''_5=R''_6=OH$; $R_7=OCH_3$; ===sb; n=2; $R_{1a}=R_{2a}=H$) in 30 ml of acetonitrile. The reaction mixture is stirred for 5 minutes at room temperature, then partitioned between saturated aqueous $NaHCO_3$-solution and ethyl acetate, the organic phase is separated, washed with saturated aqueous $NaHCO_3$-solution and several times with water, dried over $Na_2SO_4$, filtered and evaporated under vacuum. Chromatography of the residue (n-hexane/ethyl acetate=1/2) gives the title substance as a colourless foam.

Analogously as described in example 61 the following compounds are obtained in form of colourless foams ($R_1=OH$; $R_4+R_{4a}=O$; $R_7=OCH_3$; ===sb; n=2; $R_{1a}=R_{2a}=H$):

| ex: | form. | isomer | $R_2$ | $R_3$ | $R_5$ $R'_5$ $R''_5$ | $R_6$ $R'_6$ $R''_6$ | $R_{6a}$ | $R_8$ | $R_{8a}$ | start. mat. |
|---|---|---|---|---|---|---|---|---|---|---|
| 62 | III | — | —O—tBDMS | —$CH_2CH=CH_2$ | OH | OH | — | — | — | Ex. 3a |
| 63 | II | A | —O—tBDMS | —$CH_2CH=CH_2$ | OH | OH | — | — | — | Ex. 3b |
| 64 | I | A | —O—tBDMS | —$CH_2CH=CH_2$ | OH | O | | OH | H | Ex. 3c |
| 65 | III | — | —O—tBDMS | —$C_2H_5$ | $OCH_3$ | OH | — | — | — | Ex. 30 |
| 66 | I | A | —O—tBDMS | —$C_2H_5$ | $OCH_3$ | O | | OH | H | Ex. 29 |
| 67 | I | A | —O—tBDMS | —$C_2H_5$ | OH | O | | O—Im | H | Ex. 33 |
| 68 | I | A | —O—tBDMS | —$C_2H_5$ | OH | O | | O | | Ex. 50 |
| 69a | I | A | —O—tBDMS | —$C_2H_5$ | O—tBDMS | O | | —O—tBDMS | H | Ex. 58a |
| 69b | I | A | OH | —$C_2H_5$ | O—tBDMS | O | | —O—tBDMS | H | Ex. 58a |
| 69c | I | A | OH | —$C_2H_5$ | O—tBDMS | O | | OH | H | Ex. 58a |

| ex: | form. | isomer | $R_2$ | $R_3$ | $R_5$ $R'_5$ $R''_5$ | $R_6$ $R'_6$ $R''_6$ | $R_{6a}$ | $R_8$ | $R_{8a}$ | start. mat. |
|---|---|---|---|---|---|---|---|---|---|---|
| 69d | I | A | —O—tBDMS | —C$_2$H$_5$ | O—tBDMS | O | | OH | H | Ex. 58a |
| 70 | I | A | —O—tBDMS | —C$_2$H$_5$ | OH | O | | OH | H | Ex. 1c a) | a) Deprotection gives the compound of Example 6c (= Example 73)

EXAMPLE 71

Compound of formula I (R$_1$=R$_2$=R$_5$=R$_8$=OH; R$_3$=C$_2$H$_5$; R$_4$+R$_{4a}$=R$_6$+R$_{6a}$=O; R$_7$=OCH$_3$; R$_{1a}$=R$_{2a}$=R$_{8a}$=H; ≕=sb; n=2; diastereoisomer B) (deprotection)

3 ml of 40% aqueous hydrofluoric acid are added to a solution of 0.5 g of the compound of formula I (R$_1$=R$_2$O-tBDMS; R$_3$C$_2$H$_5$; R$_4$+R$_{4a}$=R$_6$+R$_{6a}$=O; R$_5$=R$_8$=OH; R$_7$=OCH$_3$; R$_{1a}$=R$_{2a}$=R$_{8a}$=H; ≕=sb; n=2; diastereoisomer B) in 30 ml of acetonitrile. The reaction mixture is stirred for 4 hours at room temperature, then partitioned between saturated aqueous NaHCO$_3$-solution and ethyl acetate, the organic phase is separated, washed with saturated aqueous NaHCO$_3$-solution and several times with water, dried over Na$_2$SO$_4$, filtered and evaporated under vacuum. Chromatography of the residue (n-hexane/ethyl acetate=1/2) gives the title substance as a colourless foam.

Analogously as described in example 71 the following compounds are obtained in form of colourless foams ($R_7 = OCH_3$; $R_{2a} = H$; ═ sb; n = 2):

| ex. | form. | isomer | $R_1$ | $R_{1a}$ | $R_3$ | $R_2$ | $R_4$ | $R_{4a}$ | $R_5$ $R'_5$ $R''_5$ | $R_6$ $R'_6$ $R''_6$ | $R_{6a}$ | $R_8$ | $R_{8a}$ | start. mat. |
|---|---|---|---|---|---|---|---|---|---|---|---|---|---|---|
| 72 | II | A | OH | H | —C$_2$H$_5$ | OH | O | | OH | OH | — | — | — | Ex. 1b |
| 73 | I | A | OH | H | —C$_2$H$_5$ | OH | O | | OH | O | — | OH | H | Ex. 1c, 8, 48 or 70 |
| 74 | III | — | OH | H | —C$_2$H$_5$ | OH | O | | OH | OH | — | — | — | Ex. 1a |
| 75 | I | C | OH | H | —C$_2$H$_5$ | OH | O | | OH | O | — | OH | H | Ex. 1e or 115 |
| 76 | III | — | OH | H | —CH$_2$CH═CH$_2$ | OH | O | | OH | OH | — | — | — | Ex. 3a or 62 |
| 77 | II | A | OH | H | —CH$_2$CH═CH$_2$ | O | | OH | O | — | OH | H | Ex. 3b or 63 |
| 78 | I | A | OH | H | —CH$_2$CH═CH$_2$ | OH | O | | OH | O | — | OH | H | Ex. 3c or 64 |
| 79 | I | C | OH | H | —CH$_2$CH═CH$_2$ | OH | O | | OH | O | — | — | — | Ex. 3d |
| 80 | III | — | —O—SO$_2$—CH$_3$ | H | —C$_2$H$_5$ | OH | O | | OH | OH | — | — | — | Ex. 4 |
| 81 | III | — | —O—SO$_2$—CH$_3$ | H | —CH$_2$CH═CH$_2$ | OH | O | | OH | OH | — | — | — | Ex. 5 |
| 82 | I | C | OH | H | —C$_2$H$_5$ | OH | O | | OH | OH | H | OH | H | Ex. 19 |
| 83 | I | B | OH | H | —C$_2$H$_5$ | OH | O | | OH | OH | H | OH | H | Ex. 20 |
| 84 | I | A | OH | H | —C$_2$H$_5$ | OH | O | | OH | OH | H | OH | H | Ex. 21 |
| 85 | II | A | OH | H | —C$_2$H$_5$ | OH | OH | H | OH | OH | — | — | — | Ex. 28 |
| 86 | III | — | OH | H | —C$_2$H$_5$ | OH | O | | OCH$_3$ | OH | — | — | — | Ex. 30 |
| 87 | I | A | OH | H | —C$_2$H$_5$ | OH | O | | OCH$_3$ | O | — | OH | H | Ex. 29 |
| 88 | I | C | OH | H | —C$_2$H$_5$ | OH | O | | OCH$_3$ | O | — | OH | H | Ex. 31 |
| 89 | I | A | OH | H | —C$_2$H$_5$ | OH | O | | O—Bz | O | — | O—Bz | | Ex. 32c |
| 90 | I | C | OH | H | —C$_2$H$_5$ | OH | O | | O—Bz | O | — | O—Im | O | Ex. 32b |
| 91 | I | A | O | | —C$_2$H$_5$ | OH | O | | OH | O | — | | O | Ex. 33 or 67 |
| 92 | I | A | OH | H | —C$_2$H$_5$ | OH | O | | OH | O | — | O—Ac | O | Ex. 52 |
| 93 | I | C | OH | H | —C$_2$H$_5$ | OH | O | | OH | O | — | O—Ac | | Ex. 51 |
| 94 | I | A | OH | H | —C$_2$H$_5$ | OH | O | | O—Ac | O | — | OH | H | Ex. 37a |
| 95 | I | A | OH | H | —C$_2$H$_5$ | OH | O | | O—Ac | O | — | OH | H | Ex. 37b |
| 96 | II | A | OH | H | —C$_2$H$_5$ | OH | OH | H | O—Ac | OH | — | — | — | Ex. 37c |
| 97 | I | C | OH | H | —C$_2$H$_5$ | OH | O | | O—Ac | O | — | O—Ac | O | Ex. 37d |
| 98 | III | — | OH | H | —C$_2$H$_5$ | OH | O | | —O—CO—O— | O | — | — | — | Ex. 34 |
| 99 | I | A | OH | H | —C$_2$H$_5$ | OH | O | | —O—CO—O— | O | — | | O | Ex. 13 |
| 100 | II | A | OH | H | —C$_2$H$_5$ | OH | O | | OH | O | — | OH | H | Ex. 14 |
| 101 | I | C | OH | H | —C$_2$H$_5$ | OH | O | | —O—COOCH$_3$ | O | — | OH | H | Ex. 28 |
| 102 | I | A | OH | H | —C$_2$H$_5$ | OH | O | | b) | O | — | OH | H | Ex. 39 |
| 103 | I | A | OH | H | —C$_2$H$_5$ | OH | O | | —O—CO—NH$_2$ | O | — | OH | H | Ex. 44 |
| 104 | I | C | OH | H | —C$_2$H$_5$ | OH | O | | —O—CO—N(CH$_3$)$_2$ | O | — | OH | H | Ex. 45 |
| 105 | I | A | OH | H | —C$_2$H$_5$ | OH | O | | —O—CO—NH$_2$ | O | — | OH | H | Ex. 46 |
| 106 | I | C | OH | H | —C$_2$H$_5$ | OH | O | | Cl | O | — | OH | H | Ex. 47b |
| 107 | I | A | OH | H | —C$_2$H$_5$ | OH | O | | Cl | O | — | OH | H | Ex. 55 |
| 108 | I | A | OH | H | —C$_2$H$_5$ | OH | O | | —OCH$_3$ | O | — | OH | H | Ex. 56 |
| 109 | I | C | OH | H | —C$_2$H$_5$ | OH | O | | —OCH$_3$ | O | — | OH | H | Ex. 53 |
| 110 | I | A | OH | H | —C$_2$H$_5$ | OH | O | | OH | O | — | OH | H | Ex. 54 |
| 111 | I | A | OH | H | —C$_2$H$_5$ | OH | OH | H | OH | O | — | OH | H | Ex. 28 |
| 112 | I | C | OH | H | —C$_2$H$_5$ | —O—CO—O— | OH | H | OH | O | — | OH | H | Ex. 15 |
| 113 | I | C | OH | H | —C$_2$H$_5$ | OH | OH | H | OH | OH | H | OH | H | Ex. 16 |
| 114 | I | C | OH | H | —C$_2$H$_5$ | OH | O | | OH | O | — | OH | H | Ex. 24b |
| 115 | I | C | OH | H | —C$_2$H$_5$ | OH | O | | —O—BOC | O | — | OH | H | Ex. 43 a) |

-continued

Analogously as described in example 71 the following compounds are obtained in form of colourless foams
($R_7 = OCH_3$; $R_{2a} = H$; ══ = sb; n = 2):

| ex: | form. | isomer | $R_1$ | $R_{1a}$ | $R_3$ | $R_2$ | $R_4$ | $R_{4a}$ | $R_5$ $R'_5$ $R''_5$ | $R_6$ $R'_6$ $R''_6$ | $R_{6a}$ | $R_8$ | $R_{8a}$ | start. mat. |
|---|---|---|---|---|---|---|---|---|---|---|---|---|---|---|
| 116 | Ib | C | OH | H | —$C_2H_5$ | OH | | O | — | — | — | O ($R'_{10} = H; X = O$) | | Ex. 47a |
| 117 | III | — | OH | H | —$C_2H_5$ | —O—CO—O— | | H | OH | OH | — | — | — | Ex. 9a |
| 118 | I | C | OH | H | —$C_2H_5$ | OH | OH | H | OH | O | O | OH | H | Ex. 24a | a) In equilibrium in solution with the hemiketal form ($R_5 + R_{8a}$ —O—; $R_8 = OH$)
a) Deprotection gives the compound of Example 6e (= Example 75)
b) $R_5 = $ —O—CO—N]—$(CH_2)_2O(CH_2)_2$—] (4-morpholinylcarbonyloxy)

The starting materials may be obtained as follows:

A) 33-O-Methanesulfonyl-24-O-tBDMS-FR 520

3 g of dimethylaminopyridine and 0.3 ml of methanesulfonic acid chloride are added to a solution of 1 g of 24-O-tBDMS-FR 520 in 40 ml of acetonitrile and stirred at room temperature for 2 hours. Then the reaction mixture is partitioned between saturated aqueous NaHCO$_3$-solution and ethyl acetate, the phases are separated, the organic phase is washed with 1N hydrochloric acid and brine, dried over sodium sulfate, filtered and evaporated under vacuum. Chromatography of the residue (n-hexane/ethyl acetate=1/1) yields the title compound as a colourless foam.

B) 33-O-Methanesulfonyl-24-O-tBDMS-FK 506

Using 24-O-tBDMS-FK 506 as starting material and proceeding analogously as described in A) gives the title compound as a colourless foam.

C) Compound of formula V ($R_1=R_2=$O-tBDMS; $R_3=C_2H_5$; $R_4+R_{4a}=$O; $R_7=$OCH$_3$; $R_9=$CH$_3$; $R_{1a}=R_{2a}=$H; ═══=sb; n=2; diastereoisomer C)

0.5 g of crown[18.6]ether and 0.7 g of 24,33-bis-O-tBDMS-FR 520 are added to a suspension of 47 mg of powdered KOH in 40 ml of tetrahydrofuran. The reaction mixture is stirred for 20 minutes at room temperature, then partitioned between 1N hydrochloric acid and ethyl acetate, the phases are separated, the organic phase is washed with brine, dried over sodium sulfate and evaporated under vacuum. The residue is redissolved in 30 ml of dichloromethane and triturated with a 1M solution of diazomethane in ether until the solution is light yellow. After evaporation of the solvent chromatography of the residue (n-hexane/ethyl acetate=2/1) gives the title compound as a colourless foam.

$^1$H-NMR (CDCl$_3$): 5.14(d,J=7.5Hz,H-26); 4.99(d,J=10Hz,H-20); 3.97(db,J=14Hz,H-6e); 3.81(s, COOCH$_3$);2.70(m,H-11).

D) Compound of formula V ($R_1=R_2=$O-tBDMS; $R_3=$CH$_2$—CH═CH$_2$; $R_4+R_{4a}=$O; $R_7=$OCH$_3$; $R_9=$CH$_3$; $R_{1a}=R_{2a}=$H; ═══=sb; n=2; diastereoisomer C)

Using 24,33-bis-O-tBDMS-FK506 as starting material and proceeding analogously as described in C) gives the title compound as a colourless foam.

E) Compound of formula V ($R_1=R_2=$O-tBDMS; $R_3=C_2H_5$; $R_4+R_{4a}=$O; $R_7=$OCH$_3$; $R_9=$CH$_3$; $R_{1a}=R_{2a}=$H; ═══=sb; n=2; diastereoisomer A)

2 g of calcium hydroxide are added to a solution of 3 g of 24,33-bis-O-tBDMS-FR 520 in 60 ml of tetrahydrofuran and 15 ml of water and stirred for 60 minutes at room temperature. Then the reaction mixture is partitioned between 0.5N hydrochloric acid and ethyl acetate, the phases are separated, the organic phase is dried and evaporated under vacuum. The residue is redissolved in 30 ml of dichloromethane and triturated with a 1M solution of diazomethane in ether until the solution is light yellow. After evaporation of the solvent chromatography of the residue (n-hexane/ethyl acetate=2/1) gives the title compound as a colourless foam.

$^1$H-NMR (CDCl$_3$) (mixture of rotamers=58/42): main rotamer: 5.20 (d,J=7.5 Hz,H-26); 4.93(d,J=10 Hz,H-20); 4.04 (db,J=13 Hz,H-6e) ;3.83 (s,COOCH$_3$). secondary rotamer: 5.13 (d,J=10 Hz,H-26); 4.70 (d, J=10 Hz,H-20); 4.57 (db, J=13 Hz,H-6e); 3.63 (s,COOCH$_3$).

Compound of formula V ($R_1=R_2=$O-tBDMS; $R_3=$CH$_2$—CH═CH$_2$; $R_4+R_{4a}=$O; $R_7=$OCH$_3$; $R_9=$CH$_3$; $R_{1a}=R_{2a}=$H; ═══=sb; =2; diastereoisomer A)

Using 24,33-bis-O-tBDMS-FK506 as starting material and proceeding analogously as described in E) gives the title compound as a colourless foam.

G) Compound of formula IV ($R_1=$O-tBDMS; $R_{1a}=R_{2a}=R_{4a}=$H; $R_2+R_4=$O—CO—O; $R_3=C_2H_5$; ═══=sb; n=2)

Using the compound of formula IV ($R_1=$O-tBDMS; $R_{1a}=R_{2a}=R_{4a}=$H; $R_2=R_4=$OH; $R_3=C_2H_5$; ═══=sb; n=2) as starting material and proceeding analogously as described in Example 13 the title compound is obtained as a colourless foam.

$^1$H-NMR-Spectra
(500 MHZ)

| Example: | spectrum: |
|---|---|
| 1a | 5.32(d, J=8.9Hz. H-29); 4.88(sb, H-26); 4.80(db, J=7.6Hz, H-20); 4.09(db. J=13Hz, H-6e); 4.03(dxd, J=2.9/9.4Hz, H-14); 4.49 (sb, H-24); 3.38/3.33/3.32(3xOCH$_3$). |
| 1b, 2a | 5.37(d, J=9.1Hz, H-29); 5.155(d, J=10.6Hz, H-26); 4.62(d, J=10.6Hz, H-20); 4.11(dxd, J=3.2/10.4Hz, H-24); 4.015(dxd, J=4.7/13.3Hz, H-6e); 3.76 (d, J=8.5 Hz, H-14); 3.42/3.375/3.370(3xOCH$_3$); 3.18(dxt, J=3.6/13.3Hz, H-6a). |
| 1c, 2b | 5.24(d, J=9Hz, H-29); 5.165(d, J=7.2Hz, H-26); 4.86(d, J=10Hz, H-20); 4.27 (dxd, J=5/13Hz. H-6e), 4.155(m, H24); 3.68(txd, J=8/2Hz, H-14); 3.504/3.406/3.404(3xOCH$_3$); 3.24(txd, J=13/3Hz, H-6a); 3.185(m, H-21); 2.955(m, H-32); 2.76(dxdxd, J=2,5/11/16Hz, H-12); 2.67(dxd, J=7/17Hz, H-23). |
| 1d | 5.39(d, J=8.3Hz, H-29); 5.09(d, J=10.5Hz. H-26); 4.84(d, J=10.1Hz, H-20); 4.37(dxd, J=4.2/12.7Hz, H-6e); 4.13(m, H-24); 3.40/3.36/3.35(3xOCH$_3$); |
| 1E, 10 | 5.37(dxq, J=9/1.3Hz, H-29); 5.18(d, J=10.7Hz, H-26); 4.73(d, J=10.8Hz, H-20); 4.37(dxd, J=4.9/13.3Hz, H-6e); 4.12(dxd, J=4.4/11.1Hz; H-24); 3.60/3.41/3.39(3xOCH$_3$). |
| 3a | 5.73(dxdxt, J=10.2/17.1/7Hz, H-37); 5.31(d, J=9.1Hz, H-29); 5.02(dxq, J=17.1/1.8Hz, H-38tr.); 4.94(dxq, J=10.2/1.8Hz, H-38cis); 4.88(s, H-26); 4.80(d, J=9Hz, H-20); 4.54(sb, H-24); 4.09(db, J=13Hz, H-6e); 4.02(dxd, J=2.7/9.4Hz, H-14); 3.38/3.34/3.21(3xOCH$_3$). |
| 3b, 12b | 5.71(dxdxt, J=10.2/17.1/6.9Hz, H-37); 5.37(d, J=8.2Hz, H-29); 5.175(d, J=10.8Hz, H-26); 5.025(dxq, J=17.1/1.8Hz, H-38tr.); 4.98(dxq, J=10.2/1.8Hz, H-38cis); 4.655(d, J=10.7Hz, H-20); 4.11(dxd, J=3/10.6Hz, H-24); 4.015 (dxd, J=4.4/13.2Hz, H-6e), 3.755(d, J=8.5Hz, H-14); 3.18(dxt, J=3.7/13.2Hz, H-6a). |
| 3c[2)] | 5.74(dxdxt, J=10/17/7Hz, H-37); 5,25(d, J=9Hz, H-29); 5.17(d, J=7Hz, H-26) |

| Example: | spectrum: |
|---|---|
| 12a[2] | 5.09(dxd, J=2/17Hz, H-38tr.); 4.99(dxd, J=2/10Hz, H-38cis); 4.89(d, J=10Hz, H20); 4.28(dxd, J=4/13Hz, H-6e); 4.15(m, H-24); 3.70(t, H-14); 3.52/2x3.42 (3xOCH$_3$); 3.26(txd, J=13/3Hz, H-6a); 2.97(m, H-32). |
| 3d, 11 | 5.71(dxdxt, J=10.1/17.1/7.0Hz, H-37); 5.37(d, J=9Hz, H-29); 5.18(d, J=10.6Hz, H-26); 5.04(dxq, J=17.1/1.9Hz. H-38tr.); 4.99(dxq, J=10.1/1.9Hz, H-38cis); 4.75(d. J=10.9Hz, H-20); 4.36(dxd, J=4.8/13.3, H-6e); 4.12(dxd, J=4.2/11Hz, H-24); 3.59/3.40/3.38(3xOCH$_3$); |
| 4[2] | 5.31(d, J=9Hz, H-29); 4.31(dxdxd, J=5/8/11Hz, H-33); 4.03(dxd, J=3/10Hz, H-14); 3.40/3.36/3.23(3xOCH$_3$); 3.06(s, O-mesyl). |
| 5[2] | 5.73(dxdxt, J=10/17/7Hz, H-37); 5.30(d, J=9Hz, H-29); 5.03(dxq, J=17/2Hz, H-38tr.); 4.96(dxq, J=10/2Hz, H-38cis); 4.51(m, H-24); 4.31(m, H-32); 4.02 (dxd, J=3/9.5Hz, H-14); 3.40/3.36/3.22(3xOCH$_3$); 3,06(s, 0-mesyl). |
| 6a, 74 | 5.27(d. J=9.1Hz, H-29); 5.09(s, H-26); 5.12(d, J=10Hz, H-20); 4.08(db, J=13Hz, H-6e); 4.02(dxd, J=5.5/9.5Hz, H-14); 3.99(m, H-24); 3.43/3.38/3.33 (3xs, 3xOCH$_3$) |
| 6b, 72 | 5.33(d, J=7Hz, H-26); 5.31(d, J=9Hz, H-29); 4.79(d, J=10Hz, H-20); 2.91 (dxd, J=7/16Hz, H-23a). |
| 6c, 73 | 5.12(d, J=9Hz, H-29); 5.115(d, J=3Hz, H-26); 5.00(d, J=10HZ, H-20); 4.30 (dxd, J=4/13Hz, H-6e); 3.87(m, H-24); 3.52(t, H-14); 3.175(m, H-21); 3.03 (m, H-32); 3.46/3.42/3.39(3xs, 3xOCH$_3$); |
| 6d[2] 71[2] | 5.36(d, J=9Hz, H-29); 5.18(d, J=9Hz, H-26); 4.80(d, J=10Hz, H-20); 4.38(d, J=13Hz, H-6e); 4.01(m, H-24); 3.50/3.42/3.38(3xOCH$_3$). |
| 6e[7], 75[7] | 5.36(d; J=9Hz; H-29); 5.18(d; J=9Hz; H-26); 4.80(d; J=10Hz; H-20); 4.38(d; J=13Hz; H-6equ.); 3.38/3.42/3.50(3xs; 3x-OCH$_3$). |
| 7c[2], 78[2] | 5.70(dxdxt, J=10/17/7Hz, H-37); 4.30(dxd, J=4/13Hz, H-6e); 3.87(m, H-24); 3.54(t, H-14); 3.03(m, H-32); 3.47/3.42/3.39(3xs, 3xOCH$_3$); |
| 9b, 15 | 4.48(dxdxd, J=12.5/2.6/0.8Hz, H-22); 4.27(dxdb, J=4.5/13Hz, H-6equ.); 3.94 (dxdxd, J=10.1/3.4/0.6Hz, H-24); 3.42/3.408/3.39(3xs, 3xOCH$_3$); 3.32(m, H-14); 3.12(txd, J=8.8/2.4Hz, H-13); 2.97(m, H-32); 2.90(d, J=9.2Hz, H-14). |
| 13 | 5.38(H-29); 4.91(H-20 and H-26); 4.33(H-24); 4.11(db, J=13Hz, H-6e); 4.04(dxd, J=2.6/9.5Hz, H-14); 3.39/3.34/3.30(3xs, 3xOCH$_3$). |
| 14 | 5.33(d, J=9.1Hz, H-29); 5.26(d, J=10.8Hz, H-26); 4.77(d, J=10.4Hz, H-20); 4.13(dxd, J=3.9/13.5Hz, H-6e); 4.08(dxd, J=2.9/10.8Hz, H-24); 1.44(d, J=6.9Hz, 11-CH$_3$). |
| 19 | 5.28(db, J=8.4Hz. H-29); 5.15(db, J=7Hz, H-26); 4.78(sb; H-20); 2.95(m, H-32). |
| 20 | 5.32(d. J=8.9Hz, H-29); 5.27(d, J=5.7Hz, H-26); 4.91(d, J=10HZ, H-20); 3.98 (d. J=4.2Hz, H-10); 1.38(d, J=6.8Hz, 11-CH$_3$). |
| 21 | 5.37(d, J=9Hz, H-29); 5.12(d. H=10.5Hz, H-26); 4.68(d, J=10.5Hz, H-20); 4.19(d, J=7.3Hz, H-10); 4.10(dxd, J=4.5/10.5Hz, H-24); 3.97(dxd, J=3.5/13Hz, H-6e); 3.51/3.43/3.39(3xs, 3xOCH$_3$); 2.96(dxdxd, J=4.518.5/11.3Hz, H-32); 1.83(d, J=1Hz, 19-CH$_3$); 1.59(d, J=1.2Hz, 28-CH$_3$); 1.33(d, J=7Hz, 11-CH$_3$); 0.83(t, J=7Hz, H-37); 0.77(d, J=6.5Hz, 25-CH$_3$); |
| 22 | 5.36(d, J=9,1Hz, H-29); 5.17(d, J=9.9Hz, H-20); 4.85(s, H-26); 4.00(dxd, J=3.7/13Hz, H-6e); 3.95(m, H-22); 3.88(dxdxd, J=2.1/4.8/10.4; H-15 or H-24); 3.66(dxd, J=2.1/11Hz, H-24 or H-15); 3.40/3.37/3.30(3xs, 3xOCH$_3$); 3.26(dxt, J=5.1/9.9Hz, H-13); 2.93(dxdxd, J=5/8/11Hz, H-32). |
| 27[4] | 5.24(d, J=9Hz, H-29); 5.14(d, J=4.2Hz, H-26); 5.0(d, J=10Hz. H-20); 4.42 (db, J=5.8Hz, H-6equ.). |
| 29 | 5.34(d, J=9Hz, H-29); 5.10(d, J=9.8Hz, H-26); 4.64(d, J=10.5Hz, H-20); 4.31 (dxd, J=4/13Hz, H-6e); 4.09(dxd, J=4.8/10Hz, H-24); 3.58(15-OCH$_3$), 3.39(32-OCH$_3$); 3.30(13-OCH$_3$); 3.16(9-OCH$_3$); 1.82(19-CH$_3$); 1.51 (28-CH$_3$), 1.18(d, J=7Hz, 11-CH$_3$). |
| 30 | 5.42(H-29); 4.99(H-20); 4.84(H-26); 4.03(db, J=12Hz, H-6e); 2.97(m, H-32). |
| 31 | 5.38(d, J=9Hz, H-29); 5.12(d, J=10.5Hz, H-26); 4.74(d, J=10.7Hz, H-20); 4.45(dxd, J=3/13Hz, H-6e); 4.12(dxd, J=4.4/10.2Hz, H-24); 3.58/3.40/3.37/3.17(4xs, 4xOCH$_3$). |
| 32a | 5.37(d, J=9Hz, H-29); 4.93(d, J=11Hz, H-26); 4.65(d, J=10Hz, H-20); 4.34 (dxd,J=3/13Hz, H-6e), 4.13(dxd, J=3/11Hz, H-24); 5.44(dxd, J=2/8Hz, H-14); 2x3.45/3.42(2xs, 3xOCH$_3$); 2.97(m, H-32). |
| 32b | 5.33(d, J=8Hz, H-29); 5.11(d, J=10.6Hz, H-26); 4.60(d, J=10.6Hz, H-20); 4.25(dxd, J=3.5/13.3Hz, H-6e); 4.11(dxd, J=3.4/10.6Hz, H-24); 5.48(d, J=8.9Hz, H-14); 3.42/3.40/3.37(3xs, 3xOCH$_3$); 2.97(m, H-32). |
| 32c | 5.47(d, J=9Hz, H-29); 5.11(d, J=11Hz, H-26); 4.58(d, J=10Hz, H-20); 4.25 (dxd, J=3/13Hz, H-6e); 4.08(dxd, J=3/11Hz, H-24); 3.60(d, J=8Hz, H-14); 3.55/3.41/3.35(3xs, 3xOCH$_3$); 2.98(m, H-32). |
| 32d | 5.42(d, J=9Hz, H-29); 5.25(b, H-26); 4.59(d, J=10HZ, H-20); 4.18(H-6e); 4.11(dxd, J=3/10Hz, H-24); 3.43/3.39/3.37(3xs, 3xOCH$_3$). |
| 33 | 8.20/7.48/7.09(imidazolyl-H); 5.37(d, J=8.9Hz, H-29); 5.27(dxd, J=2/8.8Hz, H-14); 4.88(d, J=10,5Hz, H-26); 4.62(d, J=10.3Hz, H-20); 4.34(dxd, J=4.2/13.4Hz, H-6); 4.12(dxd, J=3.5/10.2Hz, H-24); 2x3.42/3.48(2xs, 3xOCH$_3$). |
| 34 | 5.37(d, J=9Hz, H-29); 5.17(dxd, J=3/8Hz, H-14); 5.10(d, J=10.3Hz, H-26); |

$^1$H-NMR-Spectra
(500 MHZ)

| Example: | spectrum: |
|---|---|
| | 4.74(d, J=10.7Hz, H-20); 4.37(dxd, J=4.6/13.1Hz, H-6e); 4.11(dxd, J=4.2/11Hz, H-24); 2x2.13(1xs, 2xCOCH$_3$); 3.45/3.41/3.38(3xs, 3xOCH$_3$). |
| 35a | 5.38(d, J=9.1Hz, H-29); 4.76(d, J=10.8Hz, H-20); 4.43(dxd, J=3/13Hz, H-6e); 4.13(dxd, J=4/10Hz, H-24); 3.55/3.41/3.40(3xs, 3xOCH$_3$). |
| 35b | 5.39(d, J=8.9Hz, H-29); 5.13(d, J=10.4Hz, H-26); 4.79(d, J=10.1Hz, H-20); 4.14(m, H-24); 3.46/3.42/3.39(3xs, 3xOCH$_3$); |
| 36a[2] | 5.39(d, J=9.5Hz, H-29); 5.05(d, J=10.4Hz, H-26); 4.95(dxd, J=2/8Hz, H-14); 4.73(d, J=10.7Hz, H-20); 4.38(dxd, J=3/13Hz, H-6e); 4.12(m, H-24); 3.56/3.45/3.39/3xs, 3xOCH$_3$); 3.25/3.13(2xs, 2xCH$_3$SO$_2$-). |
| 36b[2] | 5.38(d, J=8.5Hz, H-29); 5.17(d, J=10.5Hz, H-26); 4.96(dxd, J=2/8Hz, H-14); 4.73(d, J=11.5Hz, H-20); 4.35(dxd, J=3/13Hz, H-6e); 4.12(m, H-24); 3.59 /3.41/3.40(3xs, 3xOCH$_3$); 3.11(s, CH$_3$SO$_2$-). |
| 37a | 5.43(d, J=8.7Hz, H-29); 5.03(m, 2H, H-14 and H-26); 4.57(d, J=10,1Hz, H-20); 4.20(dxd, J=13.6/4.7Hz, H-6e),, 4.06(dxd, J=11.8/3.3Hz, H-24); 3.52/3.39/3.30(3xs, 3xOCH$_3$); 2.16/2.13(2xs, 2xOAc). |
| 37b | 5.34(d, J=9Hz, H-29); 5.17(dxd, J=7.2/3.6Hz, H-14); 4.94(d, J=9.8Hz, H-26); 4.65(d, J=9.8Hz, H-20); 4.30(dxd, J=13.6/4.5Hz, H-6e); 4.11(dxd, J=10/3.6Hz, H-24). |
| 37c | 5.43(d, J=9Hz, H-29); 5.03(d, J=10,7Hz, H-26) 4.61(d, J=10.5Hz, H-20); 4.21(dxd, J=13.5/4.6Hz, H-6e); 4.07(dxd, J=10.7/3.3Hz, H-24); 3.61/3.40/3.33(3xOCH$_3$); 2.11(s, OAc). |
| 37d | 5.4(d; J=9.2Hz; H-29); 5.02(sb; H-26); 4.58(db; J=10Hz; H-20). |
| 39 | 5.44/5.04/4.57(3xd; J=8.2/10.8/10.1Hz, H-29/26/20); 3.74(s, -COOCH$_3$); 3.54/3.41/3.22(3xs, 3xOCH$_3$); |
| 41 | 7.93(d, J=1Hz, CHO); 5.53/5.28/4.86(3xd; J=7.9/10.4/10.6Hz, H-29/26/20); 4.37(dxd, J=13.3/4.7Hz, H-6equ.); 4.08(m, H-24). |
| 43 | 5.38(d, J=9.9Hz, H-29); 5.1(d, J=10.4Hz, H-26); 4.73(d, J=10.8Hz, H-20); 4.4(dxd, J=13.2/4.7Hz, H-6equ.); 4.12(dxd, J=7.1/4.1Hz, H-24); 1.41(s. BOC). |
| 44 | 5.43(d, J=8.9Hz, H-29); 4.98(d, J=10.8Hz, H-26); 4.58(d, J=10,4Hz, H-20); 4.22(m, H-6equ.); 4.07(dxd, J=3.3/10.9Hz, H-24); 3.54/3.41/3.23(3xs, 3xOCH$_3$). |
| 45[5] | 5.48(dxd, J=1/8.9Hz, H-29); 4.66(d, J=10.2Hz, H-20); 4.21/4.14(db/dxd; H-6equ./H-24). |
| 50 | mixture; ketone/hemiketal = 40/60<br>ketone; 5.37(d, J=8.9Hz, H-29); 4.96(d, J=10.7Hz, H-26); 4.62(d, J=10.5Hz, H-20); 4.46(d, J=10.4Hz, H-15); 4.12(dxd, J=10.5/3.3Hz, H-24).<br>hemiketal; 5.05(d, J=8.9Hz, H-29); 5.11(d, J=3.5Hz, H-26); 4.81 J=10.2Hz, H-20); 3.51(dxd, J=9.1/2.8Hz, H-15); 3.77(dxd, J=11.7/4.6Hz, H-13); 3.56(m, H-24). |
| 51 | 5.38(d, J=9.0Hz, H-29); 5.22(d, J=10.2Hz, H-26); 4.79(d, J=10.7Hz, H-20); 4.41(dxd, J=11.9/3.2Hz, H-13); 4.38(dxd, J=13/4Hz, H-6e); 4.15(dxd, J=10.7/4.3Hz, H-24); 4.08(dxd, J=9.2/3.5Hz, H-15); 3.42/3.40/3.37(3xs, 3xOCH$_3$); 3.23(dxdxd, J=10.9/8.5/5.6Hz, H-21); 3.17(txd, J=13.2/3.6Hz, H-6a). |
| 52 | mixture; ketone/hemiketal = 40/60<br>ketone; 5.38(d, J=9Hz, H-29); 4.92(d, J=10.7Hz, H-26); 4.60(d, J=10Hz, H-20); 4.47(d, J=9.5Hz, H-15).<br>hemiketal; 5.08(d, J=9Hz, H-29); 5.11(d, J=4.2Hz, H-26); 4.83(d, J=10Hz, H-20); 3.76(dxd, J=11.6/4.6Hz, H-13). |
| 58a | 5.4(dxd, J=8.9/1.1Hz, H-29); 5.12(d, J=10.8Hz, H-26); 4.57(db, J=10.5Hz, H-20); 4.24(dxd, J=13.6/4.8Hz, H-6equ.); 4.07(dxd, J=11/3.5Hz, H-24); 3.63 (d, J=8.5Hz, H-14); 3.52/3.40/3.21(3xOCH$_3$); |
| 58b | 5.34(dxd, J=8.9/1.1Hz, H-29); 4.89(d, J=10.2Hz, H-26); 4.62(d, J=10.3Hz, H-20); 4.3(dxd, J=4.3/13.8Hz, H-6equ.); 2,94(m, H-32); 2.84(dxd, H-23a). |
| 60a | 5.32(d; J=9Hz, H-29); 5.18(d, J=9.1Hz, H-26); 4.85(d, J=10.4Hz, H-20); 4.37 (db, J=10.4Hz, H-6equ.); 4.16(m, H-24); 3.44/3.41/3.36(3xs, 3xOCH$_3$); |
| 60b | 5.34(d, J=9Hz, H-26); 5.22(d, J=9.9Hz, H-29); 4.92(d, J=10,4Hz, H-20); 4.36 (db, J=11Hz, H-6equ.); 4.11(m, H-24); 3.40/3.38/3.36(3xs, 3xOCH$_3$); |
| 61 | 5.35(d, J=9Hz, H-29); 4.88(sb, H-26); 4.81(d, J=8.2Hz, H-20); 4.53(H-24); 4.11(db, J=13Hz, H-6e); 4.03(dxd, J=2.8/9.5Hz, H-14); 3.40/3.34/3.23(3xs, 3xOCH$_3$). |
| 62[2] | 5.74(dxdxt, J=10/17/7Hz, H-37); 5.34(d, J=9Hz, H-29); 4.80(d, J=9Hz, H-20); 4.54(H-24); 4.02(dxd, J=2.5/10Hz, H-14); 3.41/3.34/3.22(3xs, 3xOCH$_3$); |
| 63[2] | 5.72(dxdxt; J=10/17/7Hz, H-37); 5.41(d, J=9Hz, H-29); 5.18(d, J=10.5Hz, H-26); 5.04(dxq, J=17/2Hz, H-38tr.); 4.98(dxq, J=10/2Hz, H-38cis); 4.65(d, J=10Hz, H-20); 4.12(dxd, J=3/11Hz, H-24); 4.04(dxd, J=3/13Hz, H-6e); 3.19 (dxt, J=3/13Hz, H-6a); 3.02(m, H-32). |
| 64[2] | 5.75(dxdxt; J=10/17/7Hz, H-37); 5.28(d, J=9Hz, H-29); 5.17(d, J=7Hz, H-26); 5.09(dxd, J=2/17Hz, H-38tr.); 4.98(dxd, J=2/10Hz, H-38cis); 4.88(d, J=10Hz, H-20); 4.28(dxd, J=4/13Hz, H-6e); 4.15(m, H-24), 3.70(t, H-14); 2x3.42/3.52(2xs, 3xOCH$_3$); 3.25(txd, J=13/3Hz, H-6a); 3.03(m, H-32). |
| 65 | 5.43(d, J=8.8Hz, H-29); 4.97(d, J=9.5Hz, H-20); 4.82(H-26); 4.30(H-24); 4.04(db, J=13Hz, H-6e); 3.79/3.41/3.35/3.33(4xs, 4xOCH$_3$); |
| 67 | 8.20/7.48/7.08(imidazolyl-H); 5.37(d, J=9Hz, H-29); 5.26(dxd, J=1.9/8.9Hz, |

¹H-NMR-Spectra
(500 MHZ)

| Example: | spectrum: |
|---|---|
| | H-14); 4.86(d, J=10.6Hz, H-26); 4.60(d, J=10.3Hz, H-20); 4.34(dxd, J=4.5/13.6Hz, H-6e); 4.12(dxd, J=3.3/10.2Hz, H-24); 3.48/3.42/3.41(3xs, 3xOCH₃). |
| 68 | mixture; ketone/hemiketal = 60/40<br>ketone; 5.38(d, J=9Hz, H-29); 4.98(d, J=10.5Hz, H-26); 4.66(d, J=10.3Hz, H-20); 4.46(d, J=8.9Hz, H-15).<br>hemiketal; 5.11(d, J=9Hz, H-29); 5.13(d, J=4.4Hz, H-26); 4.87(d, J=10Hz, H-20); 3.76(dxd, J=11.4/4.4Hz, H-13). |
| 69a | 5.36(d, J=8.2Hz, H-26); 4.86(db, J=10Hz, H-29); 4.31(dxd, J=13.3/4.3Hz, H-6equ.); 4.1(dxd, J=10,2/3.6Hz, H-24); 3.54/3.41/3.32(3xs, 3xOCH₃). |
| 69c | 5.38/5.18/4.71(3xd, J=8.5/9.1/10.4Hz, H-26/29/20); 3.58/3.42/3.31(3xs, 3xOCH₃). |
| 69d | 5.42/5.13/4.59(3xd, J=9.8/10.8/10.6Hz, H-29/26/20); 4.08(dxd, J=11/3.5Hz, H-24); 3.6/3.39/3.32(3xs, 3xOCH₃). |
| 80[2)] | 4.35(dxdxd, J=5/8/11Hz, H-33); 3.41/3.37/3.34(3xs, 3xOCH₃); 3.07(s, CH₃SO₂-). |
| 81[2] | 5.73(dxdxt, J=10/17/7Hz, H-37); 5.22(d, J=9Hz, H-29); 4.34(m, H-33); 3.41/3.36/3.33(3xs, 3xOCH₃), 3.08(s, CH₃SO₂-). |
| 82 | 5.20(s, H-26); 5.17(d, J=9Hz, H-29); 4.98(d, J=9.7Hz, H-20); 4.12(H-6e); 4.10(d, J=4.6Hz, H-10); 4.04(m, H-24); 3.40/3.36/3.30(3xs, 3xOCH₃); 1.685 (d, J=1Hz, 28-CH₃); 1.66(d, J=1Hz, 19-CH₃); 1.28(d, J=6.7Hz, 11-CH₃); 0.99 (d, J=6.5Hz, 17-CH₃); 0.955(d, J=7Hz, 25-CH₃); 0.86(t, J=7.4Hz, H-37). |
| 83 | 5.10(d, J=9Hz, H-29); 5.12(s, H-26); 4.94(d, J=9.5Hz, H-20); 4.09(db, J=13Hz, H-6e); 3.94(d, J=3Hz, H-10); 3.73(m, H-24); 3.41/3.35/3.33(3xs, 3xOCH₃); 1.64(d, J=1Hz, 28-CH₃); 1.58(d, J=1Hz, 19-CH₃); 1.40(d, J=6.8Hz, 11-CH₃); 0.99 and 0.99(d and d, J=7 and 7Hz, 17-CH₃ and 25-CH₃); 0.87(t, J=7.4Hz, H-37). |
| 84[3)] | 5.22(d, J=9Hz, H-29); 5.04(d, J=6.6Hz, H-26); 4.80(d, J=10Hz, H-20); 4.15 (s, H-10); 4.00(m, H-24); 3.94(dxd, J=3/13Hz, H-6e); 3.47/3.43/3.41(3xs, 3xOCH₃); 3.05(dxdxd, J=4.3/8.8/11.3Hz, H-32); 2.85(dxd, J=7.9/16.7Hz, H-23a); 2.51(dxd, J=5.1/16.7Hz, H-23b); 2.32(m, H30); 1.74(d, J=1Hz, 19-CH₃); 1.63(d, J=1Hz, 28-CH₃); 1.29(d, J=7Hz, 11-CH₃); 0.85(t, J=7.4Hz, H-37). |
| 85 | 5.27(s, H-26); 5.16(d, J=9.1Hz, H-29); 5.13(d, J=9.5Hz, H-20); 4.07(dxd, J=4.9/13.5Hz, H-6e); 3.95(m, H-24); 3.90(m, H-22); 3.62(dxdxd, J=2.4/4.4/8.2Hz, H-15); 3.54(dxd, J=2.3/9.5Hz, H-14); 3.23(dxt, J=5/10Hz, H-13); 3.41/3.40/3.38(3xs, 3xOCH₃); 1.70(d, J=1Hz, 28-CH₃); 1.58(s, 19-CH₃); 1.10(d, J=7Hz, 11-CH₃); 0.98(d, J=7Hz, 25-CH₃), 0.95(d, J=7Hz, 17-CH₃); 0.89(t, J=7.5Hz, H-37). |
| 86 | 5.28(d, H-29); 5.27(s, H-26); 5.17(d, J=10.1Hz, H-20); 3.94(db, J=13Hz, H-6e); 3.8(m, H-24); 3.58(dxd, J=5.7/9.5Hz, H-14); 3.81(s, 9-OCH₃); 3.50 (s, 15-OCH₃); 3.41(s, 32-OCH₃); 3.34(s, 13-OCH₃); 3.10(dxdxd, J=2.5/6/10Hz, H-15); 3.02(dxdxd, J=4.3/8.8/11.2Hz, H-32); 2.30(dxt, J=3.6/13Hz, H-6a); 1.75(d, J=1Hz, 19-CH₃); 1.69(d, J=1,1Hz, 28-CH₃); 1.16 (d, J=6.9Hz, 11-CH₃). 1.10(d, J=7Hz, 25-CH₃). 0.99(d, J=6.4Hz, 17-CH₃); 0.89(t, J=7.4Hz, H-37). |
| 87 | 5.23(d, J=9Hz, H-29); 5.19(d, J=5.2Hz, H-26); 4.95(d, J=10Hz, H-20); 4.38 (dxd, J=4/13Hz, H-6e); 3.55/3.40/3.31/3.12(4xs, 4xOCH₃). |
| 88[2] | 5.30(d, J=9Hz, H-29); 5.02(d, J=8,2Hz, H-26); 4.83(d, J=9.7Hz, H-20); 4.48 (dxd, J=3/13Hz, H-6e); 3.97(m, H-24); 2x3.40/3.22/3.19(3xs, 4xOCH₃); |
| 89 | 5.28(d, J=9Hz, H-29); 5.25(d, J=6Hz, H-26); 4.84(d, J=10Hz, H-20); 4.30 (dxd, J=3/13Hz, H-6e); 4.02(m, H-24); 3.71(d, J=8Hz, H-14); 3.04(m, H-32); 3.59/3.44/3.38(3xs, 3xOCH₃); |
| 90[2)] | 5.32(d, J=8.7Hz, H-29); 5.22(d, J=6.8Hz, H-26); 4.77(d, J=10.3Hz, H-20); 4.29(db, J=13Hz, H-6e); 4.03(m, H-24); 5.45(d, J=8.6Hz, H-14); 3.44/3.43/3.38(3xs, 3xOCH₃). |
| 91 | 8.20/7.48/7.08(imidazolyl-H); 5.22(d, J=9.1Hz, H-29); 5.31(dxd, J=2.8/8.2Hz, H-14); 5.09(d, J=6.0Hz, H-26); 4.88(d, J=9.7Hz, H-20); 4.31 (dxd, J=3/12Hz, H-6e); 4.08(m, H-24); 2x3.43/3.41(2xs, 3xOCH₃); |
| 92 | mixture; ketone/hemiketal = 34/66<br>ketone; 5.25(d, J=9Hz, H-29); 5.07(d, H-26); 4.84(d, J=9.7Hz, H-20).<br>hemiketal; 5.04(d, J=9Hz, H-29); 5.15(s, H-26); 4.76(d, H-20); 3.57(dxd, J=9.8/2.6Hz, H-15); 3.75(dxd, J=11.7/4.6Hz, H-13). |
| 93 | mixture; ketone/hemiketal = 1/1.8<br>ketone; 5.25(d, J=9.2Hz, H-29); 5.08(d, J=6.6Hz, H-26); 4.85(d, J=9.6Hz, H-20).<br>hemiketal; 5.04(d, J=9.3Hz, H-29); 5.15(s, H-26); 4.76(d, J=10.2Hz, H-20); 3.57(dxd, J=10.1/2.4Hz, H-15); 3.76(dxd, J=11.7/4.5Hz, H-13). |
| 94 | 5.28(d, J=9.1Hz, H29); 5.19(d, J=5.9Hz, H26); 4.97(d, J=9.7Hz, H20); 4.40 (m, H6e); 4.29(dxd, J=8.9/4.5Hz, H13); 3.92(t, J=7Hz, H15); 3.87(m, H24); 3.41/3.39/3.38(3xs, 3xOCH₃); 3.24(m, H21). |
| 95 | 5.28(d, J=9.0Hz, H-29); 5.12(d, J=7.9Hz, H-14); 5.10(d, J=7.5Hz, H-26); 4.82(d, J=10.4Hz, H-20); 4.23(dxd, J=13/3Hz; H-6e); 4.02(t, H24); 3.50/3.41/3.30(3xs, 3xOCH₃); 2.15/2.06(2xOAc). |
| 96 | 5.20(m, 2H, H-29 and H-14); 5.10(d, J=6Hz, H-26); 4.90(d, J=9.7Hz, H-20); |

¹H-NMR-Spectra
(500 MHZ)

| Example: | spectrum: |
|---|---|
| | 4.30(dxd, J=13.3/4.5Hz, H-6e); 4.08(m, H-24); 3.45/3.44/3.41(3xs, 3xOCH₃); 3.20(m, H-21); 2.12(OAc). |
| 97 | 5.28(d, J=8.7Hz, H-29); 5.09(d, J=7.2Hz, H-26); 4.85(d, J=10.4Hz, H-20); 4.23(dxd, J=13/3Hz, H-6e); 4.05(m, H-24); 3.59/3.41/3.33(3xs, 3xOCH₃); 3.27(m, H-21); 2.05(s, OAc); |
| 98 | 5.37(d, J=5.4Hz, H-26); 5.32(d, J=8.7Hz, H-29); 4.78(d, J=10.2Hz, H-20); 4.16(dxd, J=13/3Hz, H-6e); 4.00(m, H-24); 3.42/3.38/3.36(3xs, 3xOCH₃), 2.21(s, OAc). |
| 99 | 5.31(d, J=9Hz, H-29); 5.19(d, J=6Hz, H-26); 5.08(dxd, J=5/7Hz, H-14); 4.80 (d, J=10Hz, H-20); 4.38(dxd, J=13/3Hz, H-6e); 3.81(m, H-24). |
| 100 | 5.28(d, J=9.1Hz, H-29); 4.96(d, J=10.1Hz, H-20); 4.76(d, J=4.8Hz, H-26); 4.21(m, H-24); 3.99(dxd, J=2.3/9.7Hz, H-14); 3.40/3.35/3.34(3xs, 3xOCH₃); 3.02(dxdxd, J=4.3/8.8/11.3Hz, H-32); 1.80(d, J=1Hz, 19-CH₃); 1.74(d, J=1.1Hz, 28-CH₃); 1.16(d, J=7Hz, 11-CH₃); 0.94(d, J=7Hz, 25-CH₃ and 17-CH₃); 0.87(t, J=7.4Hz, H-37). |
| 101 | 5.32(d, J=9Hz, H-29); 5.23(d, J=7.8Hz, H-26); 4.85(d, J=10.2Hz, H-20); 4.17 (dxd, J=4/13.5Hz, H-6e); 4.02(m, H-24); 3.60(m, H-15); 3.51(dxd, J=1.4/9.5Hz, H-14); 1.78(d, J=1Hz, 19-CH₃); 1.44(d, J=6.9Hz, 11-CH₃); |
| 102²⁾ | 5.09(sb, H-26); 4.99 and 4.91(d and d; J=10 and 10Hz, H-20 and H-29); 4.33 (db, J=13Hz, H-6e); 3.66(m, H-22); 3.57(m, H-24); 3.43/3.38/3.36(3xs, 3xOCH₃). |
| 103 | 5.215/5.14/4.95(3xd, J=9/5.4/10.2Hz, H-29/26/20); 4.28(dxd, J=4.5/13.7Hz, H-6equ.); 3.64/3.58/3.41/3.32(4xOCH₃). |
| 104 | 5.28/5.06/4.87(3xd, J=8.9/7.2/10.4Hz, H-29/26/20); 4.22(db, J=13.5Hz, H-6equ.); 3.33/3.42/3.56(3xs, 3xOCH₃). |
| 105 | 6.44/7.82(2xsb, 2xNH); 5.22(sb, H-26); 5.15(d, J=8.9Hz, H-29); 4.95(d, J=9.2Hz, H-20); 4.53(sb, H-6equ.); 4.18(dxd, J=4.6/13.5Hz, H-24); 3.25(q, H-21); 3.15(dxt, H-6a); 3.39/3.42/3.435(3xs, 3xOCH₃); |
| 106 | 5.26/5.08/4.88(3xd, J=9.5/6.9/10.4Hz, H-29/26/20); 4.24(dxd, J=4.4/13.5Hz, H-6equ.); 4.03(tb, H-24); 3.56/3.41/3.33(3xs, 3xOCH₃); 2.97/2.76(2xs, 2xNCH₃). |
| 107⁵⁾ | 5.32/5.13/4.97/3xd, H-26/29/20); 3.95(m, H-24); 3.36/3.39/3.42(3xs, 3xOCH₃. |
| 117 | 5.25/5.05(2xd, H-26/29); 3.31/3.36/3.42(3xs, 3xOCH₃); 3.03(m, H-32). |
| 118⁶⁾ | 5.2/5.02(m/d, H-29/26/20); 4.38(dxd, H-6equ.); 3.42/3.38/3.35(3xs, 3xOCH₃). |

¹³C-NMR-Spectra
(CDCl₃)

| Example: | spectrum: |
|---|---|
| 6f | 212.32(C-22), 202.22(C-10), 170.27(C-8), 165.04(C-1), 139.26(C-19), 3.22(C-29), 130.93(C-28); 123.57(C-20); 84.466/84.145(C-26/32); 78.475(C-13), 77.588(C-15), 76.573(C-10), 73.478/73.451(C-33/14), 72.14(C-2), 66.9(C-24), 58.816/57.042/56.483(3xOCH₃), 54.493(C-21), 46.995(C-18), 45.819(C-23). |
| 7d | 210.5/202.5/170.9/165.4/75.2(C-22/10/8/1/9). |
| 7e, 79 | 210.1/205.8/172.8/165.9/18.2(C-22/10/8/1/9). |
| 9a | 170.12/169.72(C-1/8), 150.4(O.CO.O), 138.67(C-19), 132.47(C-28), 129.62(C-29), 123.35(C-20), 96.79(C-9), 83.997(C-32). |
| 9c | 201.70(C-9), 170.14/165.05(C-1/8), 149(O.CO.O), 138.01(C-19), 131.11 (C-29), 129.50(C-28), 124.25(C-20), 83.916(C-32). |
| 16 | 199.10(C-10), 166.99/165.87(C-1/8), 152.3/149.22(O.CO.O), 138.28/ 131.02/129.68/124.16(C-19/29/28/20), 84.126(OCMe₃), 83.992(C-32), 80.535(C-9), 79.17(C-13), 78.237(C-24), 77.892(C-22), 77.524(C-15), 77.01(C-26), 73.671(C-14), 73.384(C-33), 72.137(C-2), 57.495/ 56.934/56.551(3xOCH₃), 49.047(C-18), 44.062(C-21), 38.118/37.531 C-25/C-6), 35.071/34.636/34.39(C-30/31/11), 32.647(C-16), 31.094/ 30.797/30.584(C-34/3/35); 27.97(C-12), 27.58(C-17), 25.673(C-23), 24.65 C-36), 23.304(C-5), 21.875(17-methyl), 20.818(C-4), 17.362(19-methyl), 14.783(28-methyl), 13.223(11-methyl), 11.929(C-37); 9.26(25-methyl). |
| 17 | 167.86/166.00(C-1/8), 152.41/149.72(2xO.CO.O), 137.22/133.09/128.98/ 124.98(C-19/29/28/20), 104.10(C-9), 88.88(C-10), 57.326/56.963/56.226 3xOCH₃),50.655(C-18), 46.017(C-25), 42.98(C-21), 39.997(C-6), 35.237 C-30), 35.026(C-16), 34.39(C-12), 33.991(C-31), 31.962(C-11), 31.287/31.250(C-23/34), 30.312(C-35), 26.284(C-3), 25.840(C-36), 25.383(C-17). |
| 18 | 201.51(C-10), 170.89(C-1), 164.82(C-8), 150.03(O.CO.O), 137.85/ 131.44/129.65/124.84(C-19/29/28/20). |
| 23a | 170.66/170.56(C-1/8), 149.86(O.CO.O), 138.30(C-19), 130.39(C-28), 129.80(C-29), 123.91(C-20), 84.226(C-32), 80.051(C-13), 79.23(C-9), 78.966/78.904(C-22/24). |

-continued

| | $^{13}$C-NMR-Spectra (CDCl$_3$) |
|---|---|
| Example: | spectrum: |
| 23b | 171.65/170.91(C-1/8), 149.44(O.CO.O), 138.44(C-19), 130.20(C-28), 129.36(C-29), 123.80(C-20), 84.138(C-32), 81.238(C-9), 80.48(C-13), 79.403(C-22), 79.111(C-10), 78.927(C-24), 77.25(C-14), 76.994(C-15), 75.947(C-26). |
| 24b | 172.97(C-1), 168.48(C-8), 134.4(C-19), 131.59(C-28), 128.97(C-29), 126.53(C-20), 84.166(C-32), 75.195(C-33), 58.033/56.829/56.127 (3xOCH$_3$), 48.844(C-18), 46.212(C-21). |
| 25 | 167.73/164.85(C-1/8), 149,69(O.CO.O), 136.79(C-19), 132.39(C-28), 132.39/130.73(C-28/29), 128.53(C-20), 84.111(C-32), 57.693/56.820/ 56.472(3xOCH$_3$). |
| 26a | 202.42(C-9), 171.13(C-1), 165.28(C-8), 136.11(C-19), 132.62(C-29), 131.12(C-28), 126.82(C-20), 84.113(C-32), 58.456(OCH$_3$), 56.531 (2xOCH$_3$), 49.714(C-18), 46.373(C-23-). |
| 26b | 173.74(C-1), 168.91(C-8), 137.50(C-19), 131.73(C-29), 128.58(C-28), 26.33(C-20), 84.208(C-32), 57.2/57.061/56.676(3xOCH$_3$). |
| 28 | 201.2(C-10); 168.6(C-1); 165.6(C-8); 137.4(C-19); 130.9(C-28); 128.9(0-20); 128.5(C-29). |
| 8 | 209.9/208.9/199.45/165.4/163.1(C-22/14/10/1/8) 159.04(-OCHO). |
| 42 | 208.54(C-22), 199.53(C-10), 166.42(C-1), 164.38(C-8), 158.58(OCHO), 140.28(C-19), 137.73(C-29), 130.79(C-28), 123.57(C-20), 66.243(C-26), 84.057(C-32), 76.9(C-14), 75.069(C-33), 73.417(C-2). |
| 46 | 209.27(C-22), 199.20(C-10), 167.64/163.74(C-1/8), 154.47(O.CO.N), 140.50/137.89/130.14/123.39(C-19/29/28/20), 70.206(C-2). |
| 47a | 210.32(C-22), 167.78/167.16(C-1/8), 155.54(O.CO.N), 138.79(C-19), 135 (b, C-29); 131.02(C-28), 124.43(C-20), 91.609(C-10), 84.054(C-32), 75.092(C-33), 68.584(C-24), 58.109/58.042/57.942(3xOCH$_3$). |
| 47b | 208.65/200.42(C-22/14), 167.39/164.83(C-1/8), 154.24(O.CO.N), 139.33 (C-19), 137.29(C-29), 130.71(C-28), 124.16(C-20). |
| 48 | 209.25(C-22), 169.24(C-1), 166.27(C-8), 153.41(O.CO.N), 140.69(C-19), 140.29(C-29), 129.40(C-28), 122.82(C-20), 87.968(C-26), 90.905/86.991 (C-9/10), 84.261(C-32), 61.503(15-OCH$_3$), 58.071(32-OCH$_3$), 56.677 (13-OCH$_3$). |
| 49 | 209.14(C-22), 184.68(O.CS.N), 168.92(C-1), 165.28(C-8), 141.03(C-19), 139.72(C-29), 129.43(C-28), 122.65(C-20), 95.02(C-10), 91.581(C-9), 88.676(C-26), 84.297(C-32), 82.275(C-13), 78.245(C-15), 75.575/75.432 (C-33114), 72.818(C-2), 68.016(C-24), 61.514(15-OCH$_3$), 58.238 (32-OCH$_3$), 56.806(13-OCH$_3$), 56.512(C-21), 48.776(C-23), 30.083(N-methyl). |
| 53 | 210.10/208.92/206.25(C-22/10/14), 167.39/164.05(C-1/8), 139.39/138.10/ 130.36/123.85(C-19/29/28/20), 81.232(C-9), 80.082(C-15). |
| 54 | 209.31/208.70/204.01(C-22/10/14), 167.92/163.88(C-1/8), 139.79/137.45/ 130.83/123.97(C-19/29/28120), 83.118(C-10), 67.831(C-24), 58.512/ 58.027/58.02/54.311(4xOCH$_3$). |
| 55 | 208.92(C-22), 198.98(C-10), 166.97/163.29(C-1/8), 140.66/137.29/ 131.02/123.46(C-19/29/28/20). |
| 56 | 208.89(C-22), 199.66(C-10), 165.85/164.51(C-1/8), 139.92/137.41/ 130.13/123.35(C-20/29/28/20), 70.59(C-2), 67.291(C-24), 62.863(C-9). |
| 57 | 209.55(C-22), 196.68(C-10), 166.0/164.38(C-1/8), 140.28/137.05/130.88/ 123.28(C-19/29/28120), 85.703(C-26), 84.097(C-32), 75.189(C-33), 70.389(C-2), 68.139(C-24), 62.075(C-9), 60.122/58.019/57.752(3xOCH$_3$), 56.213(C-21), 48.031(C-23), 46.862(C-18), 16.043(19-methyl), 11.14 (28-methyl). |
| 59 | 208.58(C-22), 203.72(C-10), 170.7(C-1), 163.86(C-8), 140.39/137.51/ 130.96/123.69(C-19/29/28/20), 86.028(C-26), 84.051(C-32), 80.267 (C-15), 79.691(C-13), 76.424(C-9), 75.118(C-33), 73.368(C-14), 72.925 (C-2), 68.033(C-24), 61.289/57.928/55.55(3xOCH$_3$), 56.357(C-21), 47.658 (C-18), 47.291(C-23). |
| 66 | 209.5/204.6/167.5/164.3/81.5(C-22/10/1/8/9). |
| 69b | 209.62(C-22), 204.50(C-10), 169.09/164.71(C-1/8), 140.61/135.79/130.8/ 123.44(C-19/29/28/20), 77.56(C-9), 71.403(C-2). |
| 108 | 211.33(C-22), 199.36(C-10), 166.71/164.47(C-1/8), 139.03/133.59/ 130.73/124.90(C-19/29/28/20), 85.405(C-26), 84.14(C-32), 78.99(C-13), 77.963(C-15), 75.699(C-14), 73.466(C-33), 72.245(C-2), 67.223(C-24), 64.425(C-9), 57.521/56.865/56.522(3xOCH$_3$), 55.062(C-21), 9.094(25-methyl). |
| 109 | 211.8/1197.45(C-22/10), 165.0/164.76(C-1/8), 138.26/131.68/130.93/ 123.37(C-19/29/28/20), 62.723(C-9), 9.371(25-methyl). |
| 110 | 210.07/209.53/205.85(C-22/14/10), 167.32/164.52(C-1/8), 139.69/135.58/ 130.53/123.81(C-19/29/28/20), 81.337(C-9), 72.293(C-2), 8.58(25-methyl). |
| 111 | 211.371206.86/203.55(C-22,/14/10), 167.76/164.71(C-1/8), 138.96/134.31/ 130.30/124.64(C-19/29128/20). |
| 112 | 200.24(C-10), 167.81/166.31(C-118), 149.01(O.CO.O), 138.54/129.73/ 129.13/123.57(C-19/29/28/20), 74.637(C-9), 11.737(C-37), 10.257 |

| | $^{13}$C-NMR-Spectra (CDCl$_3$) |
|---|---|
| Example: | spectrum: |
| | (25-methyl). |
| 113 | 201.74(C-10), 170.16/165.04(C-1/8), 149.25(O.CO.O), 76.213(C-9), |
| 114[6)] | 173.26/168.76(C-8/1), 138.44/131.93/129.13/126.4(C-19/29/28/20), 84.242 (C-32), 79.984/79.887/79.744(C-10/26/9), 72.737(C-2). |
| 116 | 213.24(C-22), 168.09/166.97(C-1/8), 155.52(O.CO.N), 137.69/131.32/ 130.45/123.89(C-19/29/28/20), 8.891(25-methyl) |

[1)] 250 MHz/CD$_3$OD
[2)] 250 MHz/CDCl$_3$
[3)] 500 MHz/CDCl$_3$ + CD$_3$OD
[4)] 330+ K.
[5)] 323° K.
[6)] 320° K.
[7)] 250 MHz

The compounds of the invention in free form or pharmaceutically acceptable salt form, hereinafter briefly named the "agents of the invention", possess pharmacological activity. They are thus useful as pharmaceuticals. In particular they possess antiinflammatory, and immunosuppressant and antiproliferative activity.

The antiinflammatory activity may e.g. be determined in the following test methods, wherein abbreviations have the following significance:

DNP=2,4-dinitrophenol

DNFB=2,4-dinitrofluorobenzene

TPA=12-0-tetradecanoylphorbol-13-acetate

1. Inhibition of mast cell degranulation in vitro

Murine mast cells (CFTL-12) are treated with DNP-specific IgE overnight. Degranulation is triggered by the addition of antigen (DNP) and measured as hexosaminidase activity in cell supernatant after 60 minutes in a colorimetric assay. Inhibitory substances are added 30 minutes prior to DNP.

The agents of the invention elicit in this test degranulation of mast cells (IC$_{50}$) at a dosage from about 1 ng/ml to about 50 ng/ml.

2. Oxazolone-induced allergic contact dermatitis (mouse)

[the test method is as described in F. M. Dietrich and R. Hess, Int. Arch. Allergy 38 (1970) 246–259]:

The agents of the invention elicit in this test an activity (inhibition of inflammatory swelling) of up to 58% upon a single topical application as a 0.01% solution. Hydrocortisone (1.2%) is inactive under these conditions in this model and indomethazine (3.6%) inhibits inflammation by only 22%.

3. DNFB-induced allergic contact dermatitis (the test method is as described in e.g. EP 315 978):

Two topical applications of a 0.13% formulation of the agents of the invention result in inhibition of the inflammatory reaction by up to 44%.

4. Inhibition of phorbol ester (TPA)—induced irritant contact dermatitis (mouse)

(the test method is as described in e.g. EP 315 978):

The agents of the invention elicit in this test upon single application of a 0.4–3.6% formulation an inhibition of the inflammatory reaction by up to 40%.

5. Inhibition of arachidonic acid—induced irritant contact dermatitis (mouse)

Female NMRI mice are treated topically on both the inner and outer sides of the right ear with 10 μl of DAE 244 (DMSO/acetone/ethanol=2/4/4) containing the test compound (usually 1.2 and 3.6%). After 30 minutes the right ear is treated topically with 10 μl (both inside and out) of acetone containing 1 mg of arachidonic acid. After a further 90 minutes the mice are sacrificed and the ears cut off at the cartilage line and weighed. The difference in weight between left and right ears is calculated and the % inhibition taken relative to the group treated with arachidonic acid alone.

The agents of the invention elicit in this test upon single application of a 0.4–3.6% formulation an inhibition of the inflammatory reaction by up to 30%.

6. Inhibition of ionophore (A 23187)—induced irritant contact dermatitis (mouse)

Female NMRI mice are treated topically on the inside of the right ear with 15 μl of acetone/10% DMSO containing 15 μg of A 23187 with or without the test compound (usually 0.4% and 1.2%). After 7.5 h the mice are sacrificed and the ears cut off at the cartilage line and weighed. The difference between the left and right ears is calculated for each mouse and the % inhibition is taken relative to the group having received A 23187 alone.

The agents of the invention elicit in this test upon single application of a 0.4–1.2% formulation an inhibition of the inflammatory reaction by up to 72%. Indomethazine used for comparison inhibited inflammation by 44% at 1.2% concentration.

Immunosuppressant and antiproliferative activity may e.g. be determined in the following test methods:

7. Proliferative response of lymphocytes to allogen stimulation in the mixed lymphocyte reaction (MLR) in vitro

[the test method is as described in e.g. T. Meo, "The MLR in the Mouse", Immunological Methods, L. Lefkovits and B. Pernis, Eds., Academic Press, N.Y. (1979) 227–239]:

The agents of the invention elicit in this test suppression of mixed lymphocytes (IC$_{50}$) at a dosage of from about 10 ng/ml to about 100 ng/ml.

8. Inhibition of the primary humoral immune response to sheep erythrocytes in vitro

[the test method is as described in R. I. Mishell and R. W. Dutton, Science 153 (1966) 1004–1006; R. I. Mishell and R. W. Dutton, J. Exp. Med. 126 (1967) 423–442]:

The agents of the invention are active in this test with an IC$_{50}$ of from about 0.0024 μg/ml to about 0.32 μg/ml.

9. Inhibition of proliferation of human keratinocytes (the test method is as described in e.g. EP 539326):

The agents of the invention are active in this test at concentrations of from about 3 μM/ml to about 10 μM/ml, resulting in an inhibition of from about 20% to about 50%.

10. Inhibition of phorbol ester (TPA)—induced epidermal hyperproliferation (mouse)

For induction of epidermal hyperproliferation TPA (0.005%) is applied to the pinna surface on days 1 and 3. The test compound is applied to the same sites once daily on days 1, 2, 3 and 4. The vehicle is applied in the same way to TPA-treated control animals. Evaluation of antiproliferative activity of the test compound is performed on day 4, 6 hours after the last application, by immunohistological examination of the incidence of BrdU-staining keratinocytes (BrdU injected one hour before the animals are sacrificed labels cells at the S-phase) and by measurement of the epidermal area per section area in test and control animals.

The agents of the invention elicit in this test upon 4 applications of a 0.4–1.2% formulation an inhibition of BrdU-labeling by 60–70% and an inhibition of epidermal hyperplasia by 17–42%.

The agent of Examples 71 (and 6d) and the agent of Example 93, particularly the agent of Example 71 (6d) are the preferred agents for the above indications. It has for example been determined that in the above test 6. these agents in the form of a 1.2% preparation have better activity than a corresponding 1.2% preparation of indomethazine. It is, therefore, indicated that for the above uses the compounds of Examples 71 (6d) and 93 may be administered to larger meals, for example humans, by similar modes of administration at similar or lower dosages than conventionally employed with indomethazine.

The agents of the invention are therefore useful as antiinflammatory agents and as immunosuppressant and antiproliferative agents for topical and systemic use in the prevention and treatment of inflammatory and hyperproliferative conditions and of conditions requiring immunosuppression, such as a) treatment of inflammatory and hyperproliferative skin diseases, such as atopical dermatitis, contact dermatitis and further eczematous dermatoses, seborrhoeic dermatitis, Lichen planus, Pemphigus, bullous Pemphigoid, Epidermolysis bullosa, vasculitides, erythemas, cutaneous eosinophilias, Lupus erythematosus, acne, psoriasis and cutaneous tumors;

b) prevention and treatment of allergic diseases such as extrinsic asthma, rhinitis, conjunctivitis, atopic eczema, urticaria/angioedema, food/drug allergy and anaphylaxis;

c) prevention and treatment of
  resistance in situations of organ or tissue transplantation, e.g. of heart, kidney, liver, bone marrow and skin,
  graft-versus-host disease, such as following bone marrow grafts,
  autoimmune diseases such as rheumatoid arthritis, systemic Lupus erythematosus, Hashimoto's thyroiditis, multiple sclerosis, Myasthenia gravis, diabetes type I and uveitis,
  skin manifestations of immunologically-mediated disorders; and
  alopecia areata.

The agents may be administered systemically or topically. For the above indications the appropriate dosage will, of course, vary depending upon, for example, the host, the mode of administration and the nature and severity of the condition being treated. However, in general, beneficial results are indicated to be obtained systemically at daily dosages of from about 1.0 mg/kg to about 10 mg/kg animal body weight. An indicated daily dosage in the larger mammal is in the range of from about 10 mg to about 1000 mg, conveniently administered, for example, in divided doses up to four times a day or in retard form. For topical use beneficial results are obtained upon local administration at a concentration of from about 1% to about 3% of active substance several times daily, e.g. 2 to 5 times daily.

The agents of the invention may be administered by any conventional route, in particular enterally, e.g. orally, e.g. in the form of tablets or capsules, or topically, e.g. in the form of lotions, gels, creams, sprays, and solutions such as ophthalmic or nasal solutions or aerosols for local treatment of skin and mucosal membranes, e.g. the eye, respiratory tract, vagina, oral and nasal cavity.

Pharmaceutical compositions e.g. for topical application comprising an agent of the invention in association with a least one pharmaceutically acceptable carrier or diluent may be manufactured in conventional manner by mixing with a pharmaceutically acceptable carrier or diluent. Unit dosage forms contain, for example, from about 0.0025 mg to about 50 mg of active substance.

Topical administration is e.g. to the skin. A further form of topical administration is to the eye, e.g. for the treatment of immune-mediated conditions of the eye, such as: autoimmune diseases, e.g. uveitis, keratoplasy and chronic keratitis; allergic conditions, e.g. vernal conjunctivitis; inflammatory conditions and corneal transplants, by the topical administration to the eye surface of an agent of the invention in a pharmaceutically acceptable ophthalmic vehicle.

The ophthalmic vehicle is such that the compound is maintained in contact with the ocular surface for a sufficient time period to allow the compound to penetrate the corneal and internal regions of the eye, e.g. the anterior chamber, posterior chamber, vitreous body, aqueous humor, vitreous humor, cornea, iris/ciliary, lens, choroid/retina and sclera. The pharmaceutically acceptable ophthalmic vehicle may be e.g. an ointment, a vegetable oil or an encapsulating material.

Whilst the antiinflammatory and immunosuppressant and antiproliferative activity is the main activity of the agents of the invention they also possess some degree of activity in increasing sensitivity to, or in increasing the efficacy of, chemotherapeutic drug therapy. This activity may e.g. be determined according to the test methods described in EP 360 760.

The compounds of the invention are therefore useful in reversing chemotherapeutic drug resistance of varying types, e.g. acquired or innate, or in increasing sensitivity to administered drug therapy, e.g. as a means of reducing regular chemotherapeutic dosage levels, for example in the case of anti-neoplastic or cytostatic drug therapy, as a means of decreasing overall drug toxicity and, more especially, as a means of reversing or reducing resistance, including both inherent and acquired resistance, to chemotherapy.

The invention thus also concerns the use of an agent of the invention as a pharmaceutical, particularly as an antiinflammatory, and as an immunosuppressant and antiproliferative agent; it further provides a pharmaceutical composition comprising an agent of the invention in association with at least one pharmaceutical carrier or diluent. It further provides a method of treatment of inflammatory and hyperproliferative conditions and of conditions requiring inmmunosuppression which comprises administering a therapeutically effective amount of an agent of the invention to a patient in need of such treatment.

I claim:

1. A compound of formulae I to III

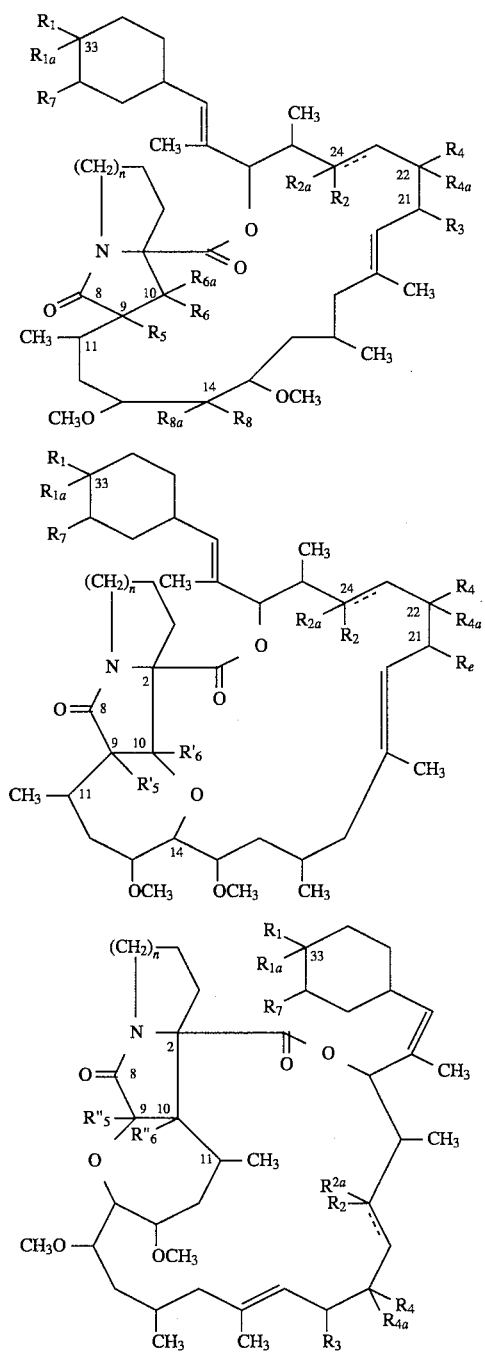

wherein
the symbol ═══ represents a single bond or, when $R_{2a}$ is absent, a double bond;

$R_1$ represents an optionally protected hydroxy group and $R_{1a}$ represents hydrogen;
or $R_1$ and $R_{1a}$ together represent oxo;

$R_2$ represents an optionally protected hydroxy group or together with $R_4$ forms the —OC(=O)O— group, and $R_{2a}$ represents hydrogen or is absent;
whereby when the symbol ═══ is a single bond, $R_2$ together with $R_{2a}$ also represents oxo;

$R_3$ represents methyl, ethyl, n-propyl or allyl;

$R_4$ represents optionally protected hydroxy or together with $R_2$ forms the —OC(=O)O— group, and $R_{4a}$ represents hydrogen;

or $R_4$ together with $R_{4a}$ represents oxo;

$R_5$ represents alkoxycarbonyloxy, halogen, optionally protected hydroxy, lower alkoxy, acyloxy or a group —OC(=X)N($R_{10}$)$R_{11}$;

or $R_5$ together with $R_{6a}$ forms a group —OC(=X)N($R'_{10}$)— attached with the nitrogen atom to the carbon atom carrying $R_{6a}$, whereby X represents oxygen or sulfur, $R_{10}$ and $R_{11}$ independently represent hydrogen or lower alkyl or together with the nitrogen atom form a five- or six-membered ring optionally containing a second heteroatom such as nitrogen or oxygen, and $R'_{10}$ is hydrogen or lower alkyl;

or $R_5$ together with $R_{8a}$ represents oxy, whereby $R_8$ represents hydroxy;

$R_6$ represents hydroxy, and $R_{6a}$ represents hydrogen or together with $R_5$ forms a group —OC(=X)N($R'_{10}$)— as defined above;

or $R_6$ and $R_{6a}$ together represent oxo;

$R'_5$ represents optionally protected hydroxy, lower alkoxy or acyloxy and
$R'_6$ represents hydroxy;
or $R'_5$ and $R'_6$ together form the —OC(=O)O— group;

$R''_5$ represents hydroxy or lower alkoxy and $R''_6$ represents hydroxy;
or $R''_5$ and $R''_6$ together form the —OC(=O)O— group;

$R_7$ represents methoxy or hydroxy;

$R_8$ represents an optionally protected hydroxy group, acyloxy, imidazolylcarbonyloxy or alkoxycarbonyloxy and $R_{8a}$ represents hydrogen;
or $R_8$ represents hydroxy and $R_{8a}$ together with $R_5$ represents oxy;
or $R_8$ together with $R_{8a}$ represents oxo; and n represents 1 or 2; in free form or salt form.

2. A compound according to claim 1 of formulae I to III as defined in claim 1, with the proviso that $R_2$ and $R_4$ are other than together the —OC(=O)O— group;

$R_4$ is other than protected hydroxy;

$R_5$ is other than alkoxycarbonyloxy, halogen, protected hydroxy, a group —OC(=X)N($R_{10}$)$R_{11}$ or together with $R_{6a}$ a group —OC(=X)N($R'_{10}$)— above;

$R'_5$ is other than protected hydroxy; and $R_8$ is other than protected hydroxy or alkoxycarbonyloxy of altogether more than 2 carbon atoms, in free form or salt form.

3. A compound according to claim 1 of formulae I to III as defined in claim 1, with the proviso that $R_4$, $R_5$ and $R'_5$ are other than protected hydroxy, and $R_8$ is other than alkoxycarbonyloxy of altogether more than 2 carbon atoms, in free form or salt form.

4. A compound of formulae I, II, or III

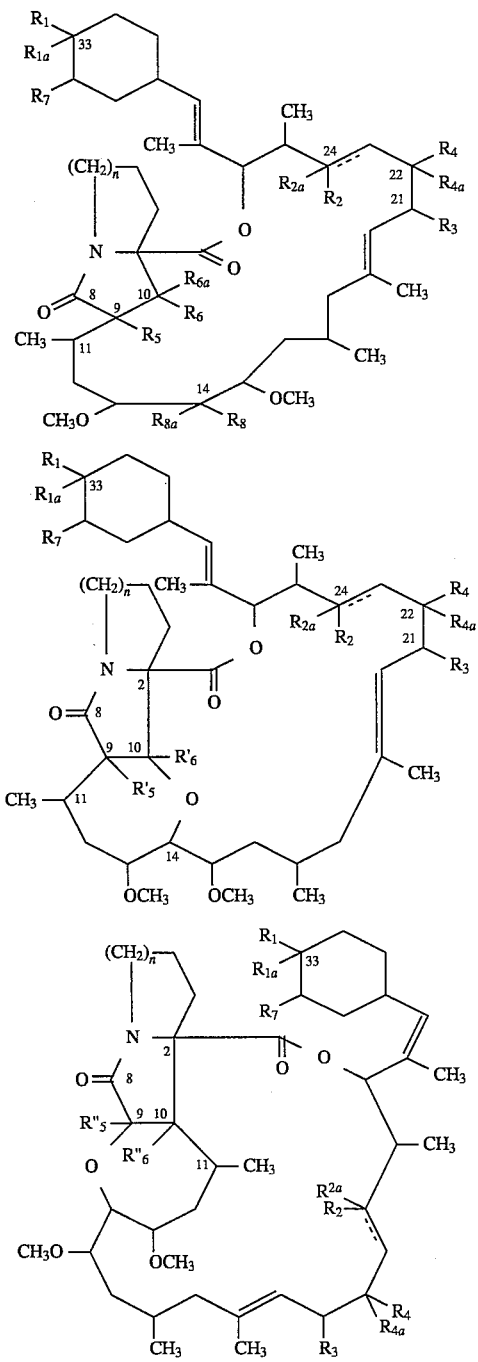

wherein the symbol ═══ represents a single bond or, when $R_{2a}$ is absent a double bond;

$R_1$ represents hydroxy or hydroxy protected by tert-butoxycarbonyl, tri($C_{1-4}$)alkylsilyl, or methylsulphonyl and $R_{1a}$ represents hydrogen;
or $R_1$ and $R_1$ together represent oxo;

$R_2$ represents hydroxy or hydroxy protected by tert-butoxycarbonyl, tri($C_{1-4}$)alkylsilyl, or methylsulphonyl or together with $R_4$ forms the —OC(=O)O— group, and $R_{2a}$ represents hydrogen or is absent; and when the symbol ═══ is a single bond, $R_2$ together with $R_{2a}$ also represents oxo;

$R_3$ represents methyl, ethyl, n-propyl or allyl;

$R_4$ represents hydroxy or hydroxy protected by tert-butoxycarbonyl, tri($C_{1-4}$)alkylsilyl, or methylsulphonyl or together with $R_2$ forms the —OC(=O)O— group, and $R_{4a}$ represents hydrogen; or $R_4$ together with $R_{4a}$ represents oxo;

$R_5$ represents ($C_{1-4}$)alkoxycarbonyloxy, halogen, hydroxy or hydroxy protected by tri ($C_{1-4}$) alkylsilyl or methylsulphonyl, ($C_{1-4}$)alkoxy, ($C_{1-4}$)alkylcarbonyloxy, formyloxy, benzyloxy or a group —OC(=X)N($R_{10}$)$R_{11}$; or $R_5$ together with $R_{6a}$ forms a group —OC(=X)N($R'_{10}$)— attached with the nitrogen atom to the carbon atom carrying $R_{6a}$, wherein X represents oxygen or sulfur $R_{10}$ and $R_{11}$ independently represent hydrogen or ($C_{1-4}$)alkyl or together with the nitrogen atom form 4-morpholinyl;

$R'_{10}$ represents hydrogen or ($C_{1-4}$)alkyl; or $R_5$ together with $R_{8a}$ represents oxy and $R_8$ represents hydroxy;

$R_6$ represents hydroxy, and $R_{6a}$ represents hydrogen or together with $R_5$ forms a group —OC(=X)N($R'_{10}$)— as defined above; or $R_6$ and $R_{6a}$ together represent oxo;

$R'_5$ represents hydroxy or hydroxy protected by tert-butoxycarbonyl, tri($C_{1-4}$)alkylsilyl, or methylsulphonyl, ($C_{1-4}$)alkoxy or ($C_{1-4}$)alkylcarbonyloxy, formyloxy, benzyloxy and $R'_6$ represents hydroxy; or $R'_5$ and $R'_6$ together form the —OC(=O)O— group;

$R''_5$ represents hydroxy or ($C_{1-4}$) alkoxy and $R''_6$ represents hydroxy; or $R''_5$ and $R''_6$ together form the —OC(=O)O— group;

$R_7$ represents methoxy or hydroxy;

$R_8$ represents hydroxy or hydroxy protected by tri ($C_{1-4}$) alkylsilyl or methylsulphonyl, ($C_{1-4}$)alkylcarbonyloxy, formyloxy, benzyloxy, imidazolylcarbonyloxy or ($C_{1-4}$) alkoxycarbonyloxy and $R_{8a}$ represents hydrogen; or $R_8$ represents hydroxy and $R_{8a}$ together with $R_5$ represents oxy; or $R_8$ together with $R_{8a}$ represents oxo; and n represents 1 or 2;

in free form.

5. A compound according to claim 4 of formulae Iq to IIIq

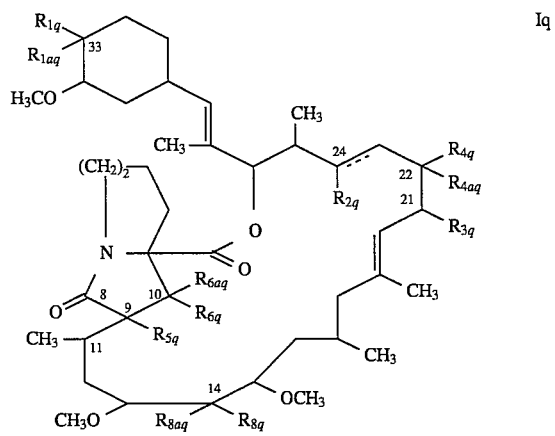

-continued

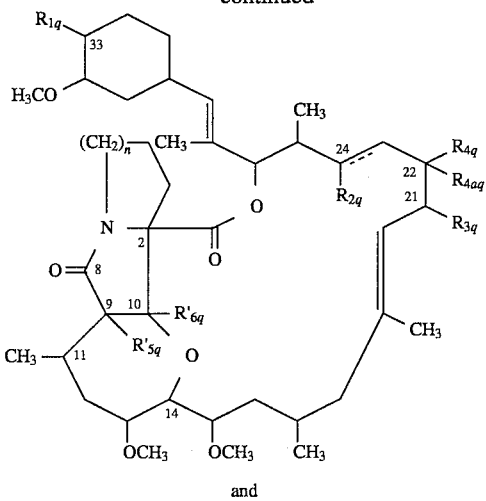

IIq and

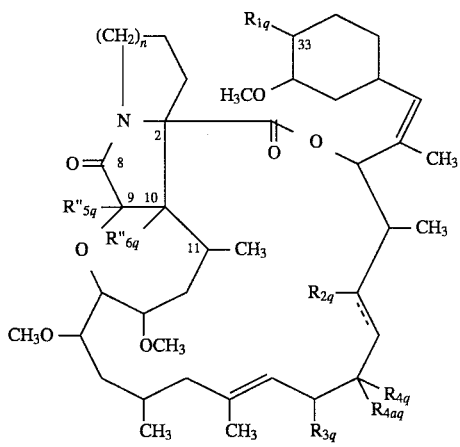

IIIq wherein $R_{1q}$ represents hydroxy optionally protected by tert-butyldimethylsilyl or methylsulfonyl and $R_{1aq}$ represents hydrogen;

or $R_{1q}$ and $R_{1aq}$ together represent oxo;

$R_{2q}$ represents hydroxy optionally protected by tert-butyldimethylsilyl or together with $R_{4q}$ forms the —OC(=O)O— group;

$R_{3q}$ represents ethyl or allyl;

$R_{4q}$ represents hydroxy optionally protected by tert-butyldimethylsilyl or together with $R_2q$ forms the —OC(=O)O— group, and $R_{4aq}$ represents hydrogen;

or $R_{4q}$ together with $R_{4aq}$ represents oxo;

$R_{5q}$ represents methoxycarbonyloxy; chlorine; hydroxy optionally protected by tert-butyldimethylsilyl, tert-butoxycarbonyl or methylsulfonyl; methoxy; formyloxy, acetoxy or benzoyloxy; or a group —OC(=O)N($R_{10q}$)$R_{11q}$ wherein $R_{10q}$ and $R_{11q}$ independently represent hydrogen or methyl or together with the nitrogen atom form 4-morpholinyl;

or $R_{5q}$ together with $R_{6aq}$ forms a group —OC(=X)N($R'_{10q}$)— and $R'_{10q}$ is hydrogen or methyl;

or $R_{5q}$ together with $R_{8aq}$ represents oxy, whereby $R_{8q}$ represents hydroxy;

$R_{6q}$ represents hydroxy, and $R_{6aq}$ represents hydrogen or together with $R_{5q}$ forms a group —OC(=X)N($R'_{10q}$)— or $R_{6q}$ and $R_{6aq}$ together represent oxo;

$R'_{5q}$ represents hydroxy optionally protected by benzoyl or acetyl and $R'_{6q}$ represents hydroxy;

or $R'_{5q}$ and $R'_{6q}$ together form the —OC(=O)O— group;

$R''_{5q}$ represents hydroxy or methoxy and $R''_{6q}$ represents hydroxy;

or $R''_{5q}$ and $R''_{6q}$ together form the —OC(=O)O— group; and $R_{8q}$ represents hydroxy optionally protected by tert-butyldimethylsilyl or methylsulfonyl; acetoxy or benzoyloxy; or 1-imidazolylcarbonyloxy; and $R_{8aq}$ represents hydrogen;

or $R_{8q}$ represents hydroxy and $R_{8aq}$ together with $R_{5q}$ represents oxy; or $R_{8q}$ together with $R_{8aq}$ represent oxo;

in free form.

6. A compound according to claim 1 of formulae Is to IIIs

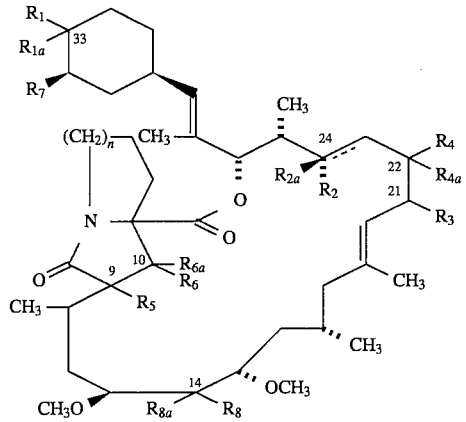

Is

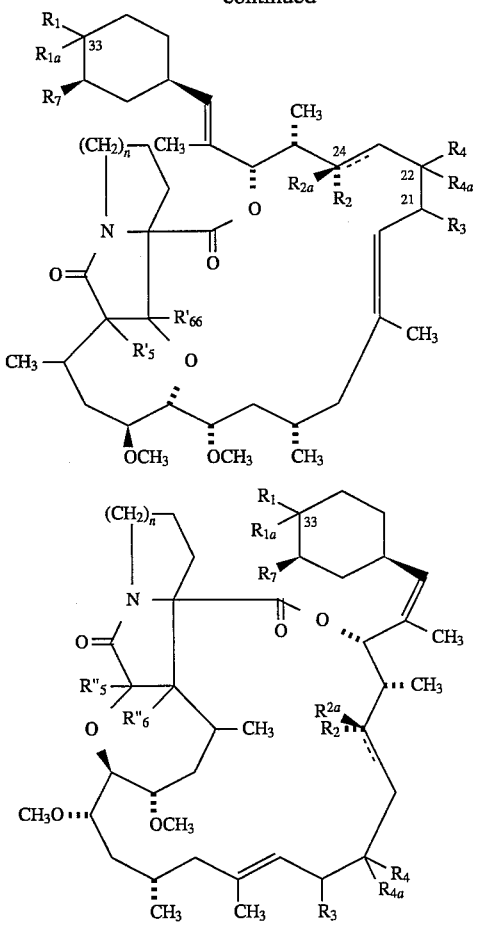

wherein the substituents are as defined in claim 1, in free form or salt form.

7. A compound according to claim 6 wherein
when $R_1$ is other than oxo together with $R_{1a}$, then $R_1$ is bound with the α-configuration to the carbon atom in 33 position;
$R_3$ preferably is bound with the α-configuration to the carbon atom in 21 position;
when $R_4$ is other than oxo together with $R_{4a}$, then $R_4$ is bound with the α-configuration to the carbon atom in 22 position;
in free form or salt form.

8. The compound of formula I according to claim 4 wherein
$R_{1a}$, $R_{2a}$ and $R_{8a}$ represent hydrogen;
$R_1$, $R_2$, $R_5$ and $R_8$ represent hydroxy;
$R_3$ represents ethyl;
$R_4$ and $R_{4a}$ together, and $R_6$ and $R_{6a}$ together, represent oxo; the symbol ═══ represents a single bond;
$R_7$ represents methoxy; and
n represents 2 diastereoisomer B.

9. The compound of formula I according to claim 4 wherein
$R_{1a}$ and $R_{2a}$ represent hydrogen;
$R_1$, $R_2$ and $R_5$ represent hydroxy;
$R_3$ represents ethyl;
$R_4$ and $R_{4a}$ together, $R_6$ and $R_{6a}$ together, and $R_8$ and $R_{8a}$ together, represent oxo;
the symbol ═══ represents a single bond;

$R_7$ represents methoxy; and n represents 2 diastereoisomer A.

10. The compound of formula I according to claim 4 wherein
$R_{1a}$ and $R_{2a}$ represent hydrogen;
$R_1$ and $R_2$ represent hydroxy;
$R_3$ represents ethyl;
$R_4$ and $R_{4a}$ together, and $R_6$ and $R_{6a}$ together, represent oxo;
$R_5$ and $R_{8a}$ together represent oxy;
$R_8$ represents hydroxy; the symbol ═══ represents a single bond;
$R_7$ represents methoxy; and
n represents 2 diastereoisomer A.

11. A compound according to claim 1 of formulae I, II, or III wherein the symbol ═══ represents a single bond or, when $R_{2a}$ is absent, a double bond;
$R_1$ represents hydroxy or hydroxy protected by tert-butoxycarbonyl, tri($C_{1-4}$) alkylsilyl, or methylsulphonyl and $R_{1a}$ represents hydrogen; or $R_1$ and $R_{1a}$ together represent oxo;
$R_2$ represents hydroxy or hydroxy protected by tert-butoxycarbonyl, tri($C_{1-4}$)alkylsilyl, or methylsulphonyl and
$R_{2a}$ represents hydrogen or is absent; and when the symbol ═══ is a single bond,
$R_2$ together with $R_{2a}$ also represents oxo;
$R_3$ represents methyl, ethyl, n-propyl or allyl;
$R_4$ represents hydroxy, and
$R_{4a}$ represents hydrogen; or
$R_4$ together with $R_{4a}$ represents oxo;
$R_5$ represents hydroxy, ($C_{1-4}$)alkoxy, ($C_{1-4}$) alkylcarbonyloxy, formyloxy, benzyloxy or
$R_5$ together with $R_8$a represents oxy, and $R_8$ represents hydroxy;
$R_6$ represents hydroxy, and
$R_{6a}$ represents hydrogen; or
$R_6$ and $R_{6a}$ together represent oxo;
$R'_5$ represents hydroxy, ($C_{1-4}$)alkoxy or ($C_{1-4}$)alkylcarbonyloxy, formyloxy, benzyloxy and
$R'_6$ represents hydroxy; or
$R'_5$ and $R'_6$ together form the —OC(═O)O— group;
$R''_5$ represents hydroxy or ($C_{1-4}$)alkoxy and $R''_6$ represents hydroxy; or
$R''_5$ and $R''_6$ together form the —OC(═O)O— group;
$R_7$ represents methoxy or hydroxy;
$R_8$ represents hydroxy, ($C_{1-4}$)alkylcarbonyloxy, formyloxy, benzyloxy imidazolylcarbonyloxy or methoxycarbonyloxy and
$R_{8a}$ represents hydrogen; or
$R_8$ represents hydroxy and $R_{8a}$ together with $R_5$ represents oxy; or
$R_8$ together with $R_{8a}$ represents oxo; and
n represents 1 or 2;
in free form.

12. A compound according to claim 1 of formulae I, II, or III in free form.

13. A compound according to claim 4 of formulae I, II or III in free form.

14. A pharmaceutical composition comprising a compound of formulae I, II or III as defined in claim 1 in free form or in pharmaceutically acceptable salt form in association with at least one pharmaceutically acceptable carrier or diluent.

15. A method of treatment of inflammatory or hyperproliferative conditions or of conditions requiring immunosuppression which comprises administering a therapeutically effective amount of a compound of formulae I, II, or III as defined in claim 1 in free form or pharmaceutically acceptable salt form to a patient in need of such treatment.

* * * * *